United States Patent [19]

Behnke et al.

[11] Patent Number: 5,801,037
[45] Date of Patent: Sep. 1, 1998

[54] EXPRESSION OF SIGNAL-PEPTIDE-FREE STAPHYLOKINASES

[75] Inventors: Detlev Behnke; Bernhard Schlott, both of Jena; Sybille Albrecht, Dresden; Karl-Heinz Gührs; Manfred Hartmann, both of Jena, all of Germany

[73] Assignee: medac Gesellschaft für klinische spezialpräparate mbH, Hamburg, Germany

[21] Appl. No.: 256,261

[22] PCT Filed: Dec. 28, 1992

[86] PCT No.: PCT/EP92/02989

§ 371 Date: Jun. 30, 1994

§ 102(e) Date: Jun. 30, 1994

[87] PCT Pub. No.: WO93/13209

PCT Pub. Date: Jul. 8, 1993

[30] Foreign Application Priority Data

Dec. 30, 1991 [DE] Germany ............ 41 43 297.7
Jun. 22, 1992 [DE] Germany ............ 42 20 516.6
Dec. 1, 1992 [DE] Germany ............ 42 40 801.6

[51] Int. Cl.$^6$ ............ C12N 9/52; C12N 15/58
[52] U.S. Cl. ............ 435/220; 435/172.3; 435/219; 536/23.2
[58] Field of Search ............ 435/220, 320.1, 435/240.1, 252.3, 252.33, 252.31, 254.11, 69.2, 69.6; 536/23.2, 23.5; 424/94.64; 514/2, 8, 12

[56] References Cited

U.S. PATENT DOCUMENTS 4,532,211  7/1985  Sako et al. ............ 435/172.3
5,336,495  8/1994  Collen et al. ............ 424/94.64
5,475,089  12/1995  Matsuo et al. ............ 530/350

FOREIGN PATENT DOCUMENTS 0 077 664  4/1983  European Pat. Off. .
0 245 444  5/1987  European Pat. Off. .
WO 93/13209  7/1993  WIPO .

OTHER PUBLICATIONS

Mitraki and King, "Protein Folding Intermediates and Inclusion Body Formation", Bio/Technology 7:690 (1989).
Kane and Hartley, "Formation of recombinant protein inclusion bodies in Escherichia coli", TIBTECH 6:95 (1988).
Enfors, "Control of in vivo proteolysis in the production of recombinant proteins", TIBTECH 10:310 (1992).
General Information/Biotechnology–derived Articles, p. 1849 Pharmacopeia vol. 23.
Papke and Blobel, "Purification of staphylokinase", Chemical Abstracts 88(5):178 (1978) Abstract No. 88:33686y.
Behnke et al, Biological Abstracts 85(6):AB–416 (1988) Abstract No. 57275.
Ferrone and Dierich eds, "Handbook of Monoclonal Antibodies", Noyes Publications, Park Ridge, NJ see Chapter 1: Monoclonal Antibody Production: Principles and Practice, pp. 1–10 (1988).
van Lijnen et al. (1991) Thrombosis & Hemostasis 66 (4): 468–473.
Wilkinson et al. (1991) Biotechnology 9: 443–448.
Kadonaga et al. (1984) J. Biological Chemistry 259: 2149–2154.
Kovacevic et al. (1985) J. Bacteriology 162: 521–528.
Behnke et al. (1987) Molecular & General Genetics 210: 528–534.
T. Sako et al., "Cloning and Expression of the Staphylokinase Gene of Staphylococcus aureus in *Escherichia coli*", *Mol. Gen. Genet.*, 190, pp. 271–277 (1983).
T. Sako et al., "Nucleotide Sequence of the Staphylokinase Gene from Staphylococcus aureus", *Nucleic Acids Research*, 11, pp. 7679–7693 (1983).
T. Sako, "Overproduction of Staphylokinase in *Escherichia coli* and its Characterization", *Eur. J. Biochem.*, 149, pp. 557–563 (1985).
I. Kondo et al., "Staphylococcal Phages Mediating the Lysogenic Conversion of Staphylokinase", *Zbl. Bakt. Suppl.*, 10, pp. 357–362 (1981).
T. Makino, "Multimolecular Form of Staphylokinase", *Zbl. Bakt. Suppl.*, 10, pp. 351–356 (1981).
I. Kondo et al., "Serotype B Staphylococcal Bacteriophage Singly converting Staphylokinase", *Infection and Immunity*, 18, pp. 266–272 (1977).
D. Gerlach et al., "Purification and Characterization of the Bacterial Plasminogen Activator Staphylokinase Secreted by a Recombinant Bacillus subtilis", *Abl. Bakt. Hyg. A,* 269, pp. 314–322 (1988).
I. Kondo, et al., "Staphylokinase Mediated by Lysogenic Conversion", *Staphylococci and Staphylococcal Infections,* pp. 529–538 (J. Jeljaszewisz & Gustav Fischer Verlag, eds., (1976).

*Primary Examiner*—Robert A. Wax
*Assistant Examiner*—Gabriele E. Bugaisky
*Attorney, Agent, or Firm*—Nixon & Vanderhye P.C.

[57] ABSTRACT

The invention relates to recombinant staphylokinase polypeptides with plasminogen activator effect and to their production and use. The polypeptides are obtained by expression of DNA sequences which are free from signal-peptide-coding regions.

8 Claims, 7 Drawing Sheets

EXPRESSION OF SIGNAL-PEPTIDE-FREE STAPHYLOKINASES

The present invention relates to signal-peptide-free expressed forms of the bacterial plasminogen activator staphylokinase (abbreviated form: SAK), including novel forms of staphylokinase, and also to processes for their production by means of genetic engineering and to their use. The invention thus includes DNA sequences which code for the SAK forms according to the invention, recombinant plasmids on which these DNA sequences are present coupled with highly effective expression signals, selected recombinant host cells which, after incorporation each time of one of these expression plasmids, are capable under cultivation conditions of the biosynthesis of the SAK forms according to the invention, and to part-processes for this cultivation and for the isolation of the staphylokinase forms (target polypeptides) from the culture soups obtained.

In conjunction with this, the invention also comprises the first-time provision of monoclonal anti-staphylokinase antibodies (anti-SAK mABs).

As has been known since the studies conducted by CH. LACK (Nature, 161 (1948), 558–560) and by K. C. ROBBINS et al. (J. Biol. Chem., 242 (1967), 2333–2342) and by K. W. JACKSON et al. (Methods in Enzymology, 80, (1981), 387), staphylokinase, a polypeptide from *Staphylococcus aureus* strains, is in the position to arrange the transformation of the proenzyme plasminogen localized in human or animal blood plasma into the fibrinolytically active enzyme plasmin, without itself displaying proteolytic activity. The mechanism of the activation is still largely unexplained.

The staphylokinase forms according to the invention are thus suitable as pharmaceutical preparations in human and also optionally in veterinary medicine during the treatment of thromboembolic angioses, while the anti-SAK mABs can be used both during the obtaining of active ingredient and, as is explained in more detail below, as pharmaceutical preparations.

Staphylokinase (molecule length: 136 amino acids) is a member of the group of those substances which can effect an activation of the fibrinolytic system via the transformation of plasminogens to plasmin and the cleavage of the fibrin caused by this. The best-known endogenous activators are the human-tissue plasminogen activator (t-PA) and urokinase. Another plasminogen activator of bacterial origin is streptokinase. The said substances are already used therapeutically for the treatment of patients with thromboembolic angioses. As the incidence of these illnesses is high, there is a considerable demand for substance quantities with a high purity standard.

Differently from the case of, say, streptokinase, no industrial production processes have been developed for SAK with the help of conventional industrial microbiology, although this bacterial plasminogen activator offers for example the advantages of a high protein stability vis-a-vis thermal and chemical influences, a tertiary structure without disulphide bridges and a small molecule size (15.8 kD).

This situation had its cause primarily in the fact that a large number of toxic accompanying products are formed by the *Staphylococcus aureus* producer strains.

After the introduction of the recombinant DNA technique, the synthesis of SAK by recombinant host organisms became possible, with the result that a technically efficient generation of pharmaceutical preparations with this polypeptide as active ingredient was realizable.

Two genes coding for staphylokinase, which have been isolated from the genomes of *Staphylococcus aureus* phages, are described in the state of the art. Used as gene donors were, on the one hand, the *S. aureus* phage C (T. SAKO et al., Mol. Gen. Genet., 190 (1983), 271–277; T. SAKO/N. TSUCHIDA, Nucl. Acids Res., 11 (1983), 7679–7693; cf. EP 0 077 664) and, on the other hand, the *S. Aureus* phage 42D (cf. DD 245 444 and also D. BEHNKE/D. GERLACH, Mol. Gen. Genet., 210 (1987), 528–534). The genes were initially primary-cloned each time on the *E. coli* plasmid pBR332 and identified by means of DNA sequence analysis after various subcloning steps.

The isolation of another staphylokinase gene has recently been described (D. COLLEN et al., Fibrinolysis, 6 (1992), 226–231). This gene, called STAR, has been obtained from chromosomal DNA of a *S. aureus* strain. All these genes naturally represent allelic variants of staphylokinase.

The gene coding for the SAK-C polypeptide was superexpressed in the *E. coli* strain WA802 after recloning into an *E. coli* expression system (EP 0 077 664; T. SAKO, Eur. J. Biochem., 149 (1985), 557–563).

The gene coding for SAK42D according to Seq. Id. No. 16, on the other hand, was cloned both onto gram-negative and also into gram-positive plasmid vectors and expressed in *Escherichia coli, Bacillus subtilis* and *Streptococcus sanguis* (see again DD 245 444 and D. BEHNKE/D. GERLACH, Mol. Gen. Genet., 210 (1987), 528–534).

The sak-STAR gene was previously expressed only under the control of its natural signals in *E. coli* (D. COLLEN et al., Fibrinolysis,, 6, (1992), 203–213).

As emerges from the cited documents, the three genes sak42D, sak-C and sak-STAR were previously brought to expression exclusively in their natural form, i.e. signal-peptide-carrying prepolypeptides were present as primary product. The synthesis of such prepolypeptides with signal sequences necessitates the secretion of the formed products into the periplasm or into the surrounding culture medium. This procedure has the substantial drawbacks that, upon a secretion into the culture medium such as occurs when using gram-positive recombinant host cells, the SAK polypeptides are exposed to the action of the extracellular proteases of these cells, with the result that there is a rapid destruction of the polypeptides.

When coliform host bacteria are used, as is described in particular in EP 0 077 664, it is attempted to circumvent this disadvantage by sluicing out the target polypeptide into the periplasmic space, as a result of which a degree of containment is achieved which is intended to offer protection against proteolytic degradation and easier access to the target polypeptide upon cell decomposition. However, this mode of expression brings other disadvantages with it, which for their part now again impede a technically efficient production of the SAK target polypeptides. This has the following causes:

The secretion of large quantities of target polypeptides (such as are necessary for a technically efficient product production) into the periplasma of gram-negative host cells overtaxes the secretory apparatus of these cells and leads to the physiological collapse of the microorganisms.

In the cultivation step of the overall process, the period of time available for expression and thus the achievable yield of the target polypeptides in question is therefore greatly reduced.

A reproducible fermentation programme is made much more difficult and as a result of this biosynthesis mode, there forms a heterologous mixture of mature SAK polypeptides and SAK prepolypeptides.

According to EP 0 077 664, the SAK-C is expressed using its natural expression signals in heterologous hosts, the consequence of which is a low level of expression for a process with adequate technical efficiency. The thermal superexpression of SAK-C as proposed by T. SAKO (Eur. J. Biochem., 149 (1985), 557–563) is characterized not only by the aforementioned problems but additionally by the disadvantage that a thermally induced protein biosynthesis under industrial fermentation conditions is manageable—if at all—at great expense and only imprecisely.

The synthesized SAK42D is isolated mainly from *B. subtilis* culture supernatant liquids according to DD 245 444. With this process, the expression and the secretion are arranged using the corresponding native control sequences of the sak42D gene by the recombinant plasmid pDB15. However, this process also has an unsatisfactory level of expression; it is furthermore characterized by a heterogeneity of the expressed SAK polypeptide and by a rapid degradation of the target polypeptide in the culture medium after prolonged cultivation (cf. D. GERLACH et al., Zbl. Bakt. Hyg., A269 (1988), 314–322).

The other natural allelic form of SAK known as SAK-STAR has also, thus far, only been heterologously synthesized using its natural signals in *E. coli* (D. COLLEN et al., Fibrinolysis, 6, (1992) 203–213), which leads to the same problems as described above for SAK-C.

The processes described thus far for the production of SAK-C, SAK42D or SAK-STAR are accordingly tied without exception to the expression of the complete natural gene sequences and inevitably suffer from the disadvantages explained above.

Against the background of the state of the art described above, the object of the invention is therefore to create processes for the technologically efficient biosynthesis of SAK polypeptides which allow the production of both highly pure and homogeneous preparations of the target polypeptide in question which are suitable for use in human or veterinary medicine during the treatment of thromboembolic angioses.

To achieve this object, it is proposed during the recombinant production of staphylokinase polypeptides with plasminogen activator effect to use such DNA sequences coding these polypeptides—i.e. such sak genes—as are free from regions which code for signal peptides. Through the removal of the nucleotide sequences which code for the signal peptides, the advantages according to the invention which are explained below, and which for the first time permit a technically efficient production of the SAK target polypeptides, are surprisingly achieved.

The signal-peptide-free polypeptides produced according to the invention collect in the inside of the cell and it has surprisingly been shown that this does not lead to the expected complications, such as in particular the formation of insoluble, biologically inactive protein aggregates (cf. Kane, J. F. et al., TIBTECH 6, p. 95 (1988), Mitraki, A. et al., Bio/Techn. 7, p. 690 (1989). Rather, the intracellularly expressed SAK target polypeptides are surprisingly present in soluble and biologically active form, with the result that the technical purification process becomes possible without complicated and costly de- and renaturing steps;

The advantages listed below are thus achieved with the process according to the invention:

The expressed SAK target polypeptides are intracellularly localized and thus readily accessible to technical processes of product concentration;

the SAK target polypeptides are present in homogeneous form, as prepolypeptides are no longer formed;

the intracellular superexpression of the SAK target polypeptides allows a long product synthesis phase; there is no physiological collapse of the cells, with the result that a high yield of SAK target polypeptides (10 to 15% of the total protein of the cells) becomes possible;

the chemical induction of the superexpression of the SAK target polypeptides, such as is possible with the expression vectors according to the invention, allows a good and simple technical manageability during the fermentation process.

It has also been shown that the SAK polypeptides intracellularly expressed according to the invention have no N-terminal methionine and are thus not to be distinguished from the naturally expressed mature secretory SAK polypeptides.

In addition to these advantages of the signal-peptide-free superexpression of the SAK target polypeptides, the target polypeptides according to the invention of the artificial allelic SAK variants according to Seq. Id. Nos. 11 and 13 and also of the SAK fragments according to Seq. Id. Nos. 7 and 9 display advantageous properties such as increased specific activity upon plasminogen activation, more rapid plasminogen activation kinetics and/or a lower molecular weight and thus a lower antigenicity. These properties have a special significance in particular for the use of the SAK target polypeptides for the treatment of thromboembolic illnesses in humans and animals.

The DNA sequences used according to the invention are thus basically characterized in that they code for signal-peptide-free mature native staphylokinase and for allelic SAK variants or SAK fragments which equally have the known plasminogen activator effect of the native molecule, and additionally in that each time, the translation-initiation codon ATG is connected immediately upstream from their 5'-end.

Preferred for the achievement of the object of the invention are such DNA sequences of the type explained above as have either the nucleotide sequence according to Seq. Id. No. 1 or the nucleotide sequences of allelic variants or fragments of the sequence according to Seq. Id. No. 1. In particular—besides the nucleotide sequence according to Seq. Id. No. 2—the nucleotide sequences according to Seq. Id. No. 3 and Seq. Id. No. 5, which are natural allelic variants of the primary nucleotide sequence according to Seq. Id. No. 1, are also used for this purpose.

The nucleotide sequence according to Seq. Id. No. 1 represents the natural sak42D structure gene, linked according to the invention at the 5'-end now with the ATG start codon and at the 3'-end with the termination codon TAA.

The sak42D structure gene can be provided for the requirements of the present invention on the recombinant starting plasmid pMET5 (FIG. 1). Plasmid pMET5—a derivative of the customary cloning vector pUC19—carries a DNA section which codes for the sak42D gene and which has been isolated from one of the plasmids, known from the literature, of the pDB family (see DD 245 444 or D. BEHNKE/D. GERLACH, Mol. Gen. Genet., 210 (1987), 528–534), preferably from pDB15 or pDB17, by means of process steps known per se of the recombinant DNA technique. In detail, plasmid pMET5 carries the section of the native sak42D gene characterized in Seq. Id. No. 16 by the nucleotide sequence 436 to 1023. Missing from this section at the 5'-end compared with the sak42D sequence (cf. the complete sequence as given in Seq. Id. No. 9) for example on pDB17 are the native 5'-flanking regulatory regions, the coding sequence for the signal peptide and the codons for the first four amino acids of the mature SAK42D; the latter have been separated from the original gene by a TaqI restriction endonucleose cut (at this 5'-end, in the pMET5-DNA a unicalar SalI-cleavage point has been formed instead of this). Downstream from the sequence coding for SAK42D, the 3'-flanking non-coding regions of the primarily isolated sak42D-DNA and sections of the DNA of *E. coli* plasmid pBR322 are however still contained on pMET5 as on pDB17.

For the purposes of the present invention, the reconstitution of the sak42D gene section of plasmid pMET5 to the signal-peptide-free coding sequence for mature native SAK42D, as is represented in Seq. Id. No. 1 can take place by the adding-on of a chemically synthesized linker pair with the corresponding specific nucleotide sequence.

In an analogous manner, through individual steps known per se of the recombinant DNA technique which expressly include the linking of chemically synthesized linker molecules, the further natural and artificial allelic forms and fragments of the sak-DNA sequences according to the invention can be produced from the sak42D-DNA section removable from the plasmid pMET5, in particular a) those two DNA sequences with the nucleotide sequences according to Seq. Id. Nos. 3 and 5 which—embedded as mentioned between ATG start codon and termination codon—are the structure genes for the natural allelic variants known thus far of the native mature SAK polypeptide, furthermore b) those two DNA sequences with the nucleotide sequences according to Seq. Id. Nos. 7 and 9 which are the signal-peptide-free structure genes for novel N-terminally shortened fragments of the native mature polypeptide SAK42D, and finally c) those two DNA sequences with the nucleotide sequences according to Seq. Id. Nos. 11 and 13 which represent signal-peptide-free structure genes for novel artificial allelic variants of the native mature polypeptide SAK42D.

The DNA sequences described above, in particular the DNA sequences listed in the sequence protocol under the Seq. Id. Nos. 1 to 7, can be introduced into procaryotic or eucaryotic host cells in a manner known per se and be expressed there as signal-peptide-free staphylokinase forms with plasminogen activator effect.

Supplementarily to the aforementioned DNA sequences, preferably to the DNA sequences mentioned in the sequence protocol under the Seq. Id. Nos. 1, 3, 5 and 7, the subject-matter of the invention also includes in this sense all those DNA sequences which, after introduction into suitable pro- or eucaryotic host cells, guarantee the expression of polypeptides which have at least a part of the primary structure in quest ion and one or more of the biological or immunogenic properties of the SAK polypeptides according to the invention. Included in particular are a1) Such DNA sequences as hybridize with the SAK-polypeptide-coding regions of the DNA sequences described above, preferably with the DNA sequences listed in the sequence protocol under Seq. Id. Nos. 1, 3, 5, 7, 9, 11 and 13 or with fragments of same, under standard conditions (see below) and also b1) Such DNA sequences as, with the exception of the deviations caused by the degeneration of the genetic code, hydbridize for their part with the DNA sequences named under a).

According to the invention, standard conditions are those under which the hybridization is carried out at temperatures between 55° and 68° C. and a salt concentration of 5×SSC buffer.

According to the invention, the DNA sequences summarized under a) or a1) include such as carry the so-called silent mutations enclosed in the nucleotide sequences according to Seq. Id. Nos. 1, 3, 5, 7, 9, 11 and 13, i.e. display selective nucleotide exchanges which do not however bring after them any change in the amino acid sequence of the corresponding staphylokinase form in each case.

In the present invention, all the DNA sequences according to the invention are preferably introduced into the suitable pro- and/or eucaryotic host cells by means of transformation. The invention accordingly includes in particular expression plasmids which contain the DNA sequences according to the invention operatively linked with expression control sequences.

According to the invention, those DNA sections of the expression plasmids in which each time a combination of sak structure gene according to the invention and ATG start codon plus TAA termination codon is coupled to expression control sequences is kept free from regions which code for signal peptides.

In this way, the sak-recombinant expression plasmids used in the present invention guarantee the signal-peptide-free and thus intracellular expression of the target polypeptides in the host cells used each time.

In connection with the invention, sak-recombinant expression plasmids built up from procaryotic DNA are used exclusively, especially such as whose expression boxes (totality of the expression signals as described in detail below) contain the sak genes according to Seq. Id. Nos. 1 to 13, operatively linked with procaryotic control sequences, if host cells of procaryotic origin are provided for the expression of the SAK polypeptides according to the invention.

It has proved expedient for the present invention to arrange the following combination of procaryotic control sequences in the expression boxes of the vectors—viewed in direction of reading:

tac promoter plus binding sequence for the lac repressor, translation-initiation region, in the form of a tandem arrangement of Shine-Dalgarno sequences with defined spacers, transcription terminator.

(Abbreviated form of such a combination:
R;tac;SD;T-configuration).

The sak sequences according to the invention, which—as described—are each time already linked with the ATG start codon and with a TAA codon, are introduced fittingly into such R;tac;SD;T-configurations.

Within the framework of the present invention, particularly high expression performances can be achieved upon the incorporation of boxes with such R;tac;;SD;T-configurations if they contain the DNA sequence according to Seq. Id. 15 as translation-initiation sequence.

According to the invention, it has also proved extraordinarily advantageous from the aspect described above to use in combination both expression plasmids from bacterial DNA and bacteria cells—preferably gram-negative bacteria, in particular *E. coli* strains, but also strains of the species Bacillus—as host cells. A highly efficient expression of the signal-peptide-free SAK target polypeptides according to the invention is to be achieved with such bacterial expression systems. Particularly advantageous effects were achieved during the synthesis of the SAK target polypeptides according to the invention in *E. coli* expression systems. For this preferred version of the invention, expression plasmids were constructed which, besides features such as replication origin, selective marker and polylinker region a) have expression boxes with a R;tac;SD;T-configuration in which the DNA sequences incorporated each time according to Seq. Id. Nos. 1, 3, 5, 7, 9, 11 and 13 are linked directly with the translation-initiation region according to Seq. Id. No. 15, and b) which derive from customary E. coli cloning or expression vectors, preferably from the pUC and the pMEX vectors.

Examples of expression plasmids produced according to the invention which carry the sak genes are (see also FIGS. 2 and 3 and Examples 3, 4, 7, 8):

pMEX602sak
pMEX6ΔN10sak
pMEX6ΔN14sak
pMEX6sakM26C
pMEX6sakM26L

Plasmids of the pUC, pBR and p 15A types can accordingly also be used.

E. coli host cells were each time transformed according to standard protocol with these E. coli expression plasmids according to the invention.

For the intracellular expression of the SAK target polypeptides, E. coli receptor strains such as for example JM101, K12 or C600 can be used in this preferred expression system. Particularly good expression results were achieved when using E. coli TG1 host cells.

Examples of recombinant strains produced according to the invention are (cf. Examples 3, 4, 7, 8)

E. coli TG1 (pMEX602sak), E. coli TG1 (pMEX6ΔN10sak), E. coli TG1 (pMEX6ΔN14sak), E. coli TG1 (pMEX6sakM26C), E. coli TG1 (pMEX6sakM26L).

The aforementioned strains are examples of such host cells as display the advantages according to the invention, namely:

they express the sak genes according to the invention correctly and at a high level (see also FIG. 4a), they realize a completely intracellular product formation and enrich the target polypeptides each time in the cytoplasm of the host cells (target polypeptide is not sluiced out into the periplasmatic space of the cells), each time, they synthesize and accumulate a soluble and biologically active target polypeptide, they react in culture effectively on the algorithm of the chemical induction and they prove to be adequately stable recombinant microorganisms also for large-scale fermentations as well as for high-cell-density processes with which the necessary high yields of target polypeptides for an efficient technical obtaining of product can be achieved (up to 15% of the total protein of the host cells).

Moreover, it was surprisingly found that the E. coli TG1 strains used according to the invention synthesize SAK forms which have no N-terminal methionine in their amino acid sequence.

The cultivation of the sak-recombinant host cells according to the invention—in particular of the recombinant E. coli TG1 strains—takes place under sterile and aerobo-submerse conditions in a manner known per se in the stages of the pre- and main cultures each time in a nutrient medium with assimilable carbon and nitrogen sources and also with a defined mineral salts content.

According to a particularly preferred version of the invention, the sak-recombinant E. coli TG1 strains are subjected to a fermentation process which is additionally characterized in that the cultivation is carried out at temperatures between 28° C. and 42° C. for the period of 4 hours to 16 hours in a full medium or a so-called synthetic medium, each time with addition of 50 mg/l to 100 mg/l ampicillin, and 2 to 4 hours after the start of fermentation, the biosynthesis of the recombinant target polypeptide by the host cells is started by means of addition of isopropyl thiogalactopyranoside (IPTG) to the medium up to a final concentration of 0.3 mmol/l when the biomass has reached a cell density of ca. 0.2 to 1.0 A600 units.

The SAK target polypeptides are preferably isolated from the host cells in the following way: The host cells are decomposed, preferably with ultra-sound, and the soluble portions of the decomposed material are separated from the insoluble portions. The soluble portions are then conducted direct to an ion exchanger. In the next step, the target polypeptide is selectively eluted from the ion exchanger with an aqueous NaCl solution. The eluate is advantageously passed direct to a hydrophobic interaction chromatography after single enrichment with NaCl. Finally, the target polypeptide is eluted from the hydrophobic interaction chromatography medium with high selectivity by a falling NaCl gradient and subsequently obtained from the eluate. This purification of the target polypeptide from lysates of recombinant E. coli TG1 cells is efficient in a particular way through the simple possibility of the buffer adaptation between the two purification stages.

The abovementioned treatment process is particularly efficient if the NaCl concentrations in the first elution step are between 30 and 500, preferably 200 to 300 mM, are increased to 2.0 to 3.0M prior to feeding to the hydrophobic interaction chromatography and, appropriately for the falling NaCl gradient, an initial concentration of 2.0 to 3.0M is chosen which is guided falling to a final concentration of 15 to 100 mM (see also FIG. 5).

The treatment process described above permits, in only two chromatography steps, a separation of the target polypeptides which is as inexpensive as it is easily performable in technical terms. The latter are obtained in a highly pure form and chromatographically homogeneously in this process. The purification process is easily extendable to industrial scale. This process also permits a gentle, low-loss treatment (without de- and renaturing steps) of the SAK target polypeptide obtained in the crude cell lysate. The fact that, in the fermentation stage of the invention, the target polypeptides are not present as a mixture of pre-polypeptides and mature target polypeptides is particularly advantageous for the described purification process.

In addition to the already-known natural allelic staphylokinase forms such as SAK42D, SAK-C and SAK-STAR, specific novel SAK forms are also made available for the first time within the framework of the invention which have advantageous properties, in particular the SAK fragment form N10ΔSAK42D with the amino acid sequence according to Seq. Id. No. 7, the artificial allelic SAK form SAKM26C with the amino sequence according to Seq. Id. No. 11 and the artificial allelic SAK form SAKM26L with the amino sequence according to Seq. Id. No. 13.

With the fragment forms N10ΔSAK42D and N14ΔSAK42D, N-terminally shortened SAK polypeptides with plasminogen activator effect are present; their molecule lengths are 126 and 122 amino acids respectively.

The artificial allelic forms SAKM26C and SAKM26L represent for the first time methionine-free SAK forms with plasminogen activator effect; they have the molecule length of 136 amino acids.

Accelerated activation kinetics for plasminogen were surprisingly found for the fragments. The reduced molecule size also suggests a lower antigenicity.

Besides a specific activity which is some cases was two-fold higher (cf. Table 2), accelerated activation kinetics for plasminogen were also found for the artificial allelic forms. These new properties make the SAK fragments or the artificial allelic SAK forms particularly attractive for therapeutic use for the treatment of thromboembolic illnesses in humans and animals.

The present invention also includes monoclonal antibodies against staphylokinase. Previously, only polyclonal anti-SAK antibodies were available (cf. T. SAKO/N. TSUCHIDA, Nucl. Acids Res., vol. 11 (1983), 7679–7693, and D. GERLACH et al., Zbl. Bakt. Hyg., vol. A269 (1988), 314–322). With recourse to pure SAK42D polypeptide, which has preferably been produced with recombinant E. coli host cells, hybridoma cell lines forming anti-SAK antibodies were obtained for the first time according to modified KÖHLER/MILSTEIN methods.

Two of these cell lines—they bear the designations alpha-SAK IG8/H6 (deposited as ZIM 0511, transferred into DSM ACC2100) and alpha-SAK IIA4/A10 (deposited as ZIM 0512, transferred into DSM ACC2101)—were used for in vitro cultivation and the monoclonal anti-SAK antibodies IG8/H6 and IIA4/A10 have been isolated from the culture supernatant liquids in a manner known per se by immune-affinity chromatography. These monoclonal antibodies are in the position to inactivate the plasminogen activator properties of the SAK forms according to the invention (cf. Example 17).

Using this property, the anti-SAK mABs according to the invention can be used a) in test systems for the detection of staphylokinase in microbiological and in medical diagnosis, for example
   a1) for the qualitative detection of SAK in sample liquids by means of Western blotting or immune precipitation and
   a2) in ELISA test systems for the quantitative detection of SAK in sample liquids, as well as
b) for the direct preparation in pure form of SAK polypeptides from fermentation broths or crude extracts by means of immune-affinity chromatography. The latter creates an alternative possibility for a highly efficient treatment process.

Because of their plasminogen activator property, the SAK polypeptides produced according to the invention, both the natural allelic SAK forms which for the first time are signal-peptide-free and thus intracellularly synthesized and the novel artificial allelic SAK forms or fragments, are excellent active ingredients for use in pharmaceutical compositions for the treatment of thromboembolic illnesses.

Coming into question in particular for this purpose are such pharmaceutical compositions as those in which one or more SAK forms synthesized by the process according to the invention are contained in combination with pharmaceutically compatible diluents, adjuvants and/or carrier substances. The formulations are preferably provided for parenteral, and in a particularly preferred manner for intravenous injection. Preferred dosage quantities lie in the range from 3 to 100 mg polypeptide per injection.

The monoclonal anti-SAK antibodies according to the invention are also valuable active ingredients in anti-dot preparations, i.e. in preparations for the inhibition of unwanted strong plasminogen activation by staphylokinase. The present invention thus also includes pharmaceutical compositions which contain such antibodies, optionally in combination with pharmaceutically compatible diluents, adjuvants and/or carrier substances.

In connection with the present invention, biologically pure samples of

| Plasmid pMET5 | (DSM 6841) |
| Hybridoma cell line alpha-SAK IG8/H6 | (ZIM 0511) |
| | (DSM ) |
| Hybridoma cell line alpha-SAK IIA4/A10 | (ZIM 0512) |
| | (DSM ) | have been deposited at the German Collection for Microorganisms (DSM), Mascheroder Weg 1B, D-3300 Brunswick. Recourse was also had to the following deposited plasmids or receptor strains:

| Plasmid vector pUC19 | (DSM 3425) |
| Receptor strain E. coli TG1 | (DSM 6056). |

The invention will be explained below by means of a detailed description of preferred versions relating to the construction of the sak genes according to the invention, expression plasmids and host cells and by means of embodiments.

The oligonucleotide linkers used in the examples are listed in Table 1.

BRIEF DESCRIPTION OF THE DRAWINGS

FIG. 4A. Representation of the super-expression of the described staphylokinase polypeptides by means of a gel from the SDS-PAGE of crude cell lysates. FIG. 4B. Representation of the binding of the monoclonal antibody IG8/H6 to all the described staphylokinase polypeptides by means of a Western blot of the crude cell lysates separated in FIG. 4A.

According to a preferred version of the invention, the procedure comprises the part-steps given below:

PART-STEP A

Construction of a base plasmid coding the mature SAK42D (plasmid designation: pTZ19Rsak1).

Figure 1:
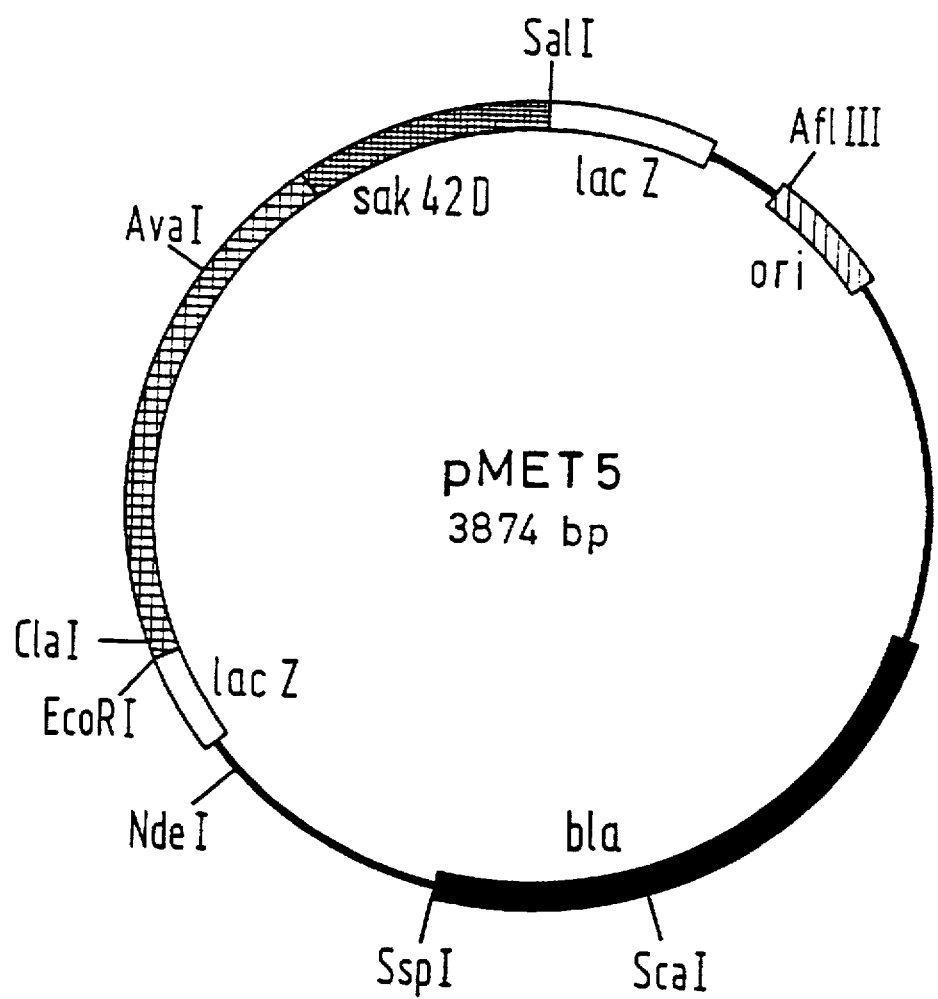
FIG. 1: Gene and restriction map of the plasmid pMET5.

The recombinant plasmid pMET5 (FIG. 1) is used as gene donor DNA for the construction of the base plasmid pTZ19Rsak1 coding the mature SAK42D. The former was constructed from the plasmid pDB17 by a series of genetic engineering operating steps.

The reconstitution of the complete coding sequence for mature SAK42D including the introduction of portable translation signals (ribosome binding sequence (RBS) and ATG start codon) and of a transition sequence to the expression connection of the sak42D gene to a suitable transcription signal (promoter) takes place by the adding-on of a chemically synthesized linker pair upstream from the unicalar SalI site. To this end, pMET5 is opened first at the unique SalI site and according to the invention the linker pair L1/L2* which is semi-phosphorylated by means of T4-polynucleotide kinase (compare Table 1; * in the following description indicates the phosphorylated linker partner), which develops compatible ends to SalI and HindIII intersections upon annealing, ligates by means of T4-DNA ligase to the ends of the linearized plasmid pMET5. Through subsequent HindIII digestion, a ca. 1.2 kb large SAK42D-coding fragment flanked on both sides by HindIII ends is obtained, which is intermediately cloned in the HindIII site of the commercial vector plasmid pTZ19R (USB, Bad Homburg). In the process there forms, inter alia, the plasmid pTZ19Rsak0 with in-frame orientation of the sak42D gene to the lac gene of the vector plasmid.

To separate the 3'-flanking DNA sections not coding for SAK42D, the 1.2 kb large EcoRI/HindIII fragment is isolated from pTZ19Rsak0 first and from this is obtained in a favourable manner, by consecutive restrictase digestion with AvaI, AvaII and HinfI, a 388 bp large EcoRI/HinfI fragment, in which the last 27 bp of the sequence coding for SAK42D have also been removed by the HinfI cut. To reproduce the complete sequence at the 3'-end of the sak42D gene, the linker pair L3*/L4 adaptable to HinfI and PstI ends (cf. Table 1) is added on in a manner known per se to the HinfI terminus of the EcoRI/HinfI fragment. The thus-forming 433 bp large EcoRI/PstI fragment with the now-complete sak42D structure gene is in turn inserted into the vector plasmid pTZ19R which had previously been treated with the same enzymes.

The thus-produced plasmid pTZ19Rsak1 acts as base plasmid for the following genetic engineering process steps for the production of expression vectors for SAK42D and N-terminally shortened SAK42D forms.

PART-STEP B
Construction of expression vectors for SAK42D and N-terminally shortened SAK42 polypeptides The commercial plasmids pMEX5 and pMEX 6 (both medac, Hamburg) are used as expression vectors, in which the expression is arranged by the synthetic tac promoter and transcription is stopped by the two tandem transcription terminators rrnBT1 and rrnBT2. The genes to be expressed are inserted between the regulation signal sequences (hereinafter called R;tac;SD;-;rrnBT1T2 arrangement). The two said plasmids differ from each other only in that they contain the region additionally making possible the formation of single-stranded DNA from the E. coli-f1 phages in different orientation.

Figure 3:
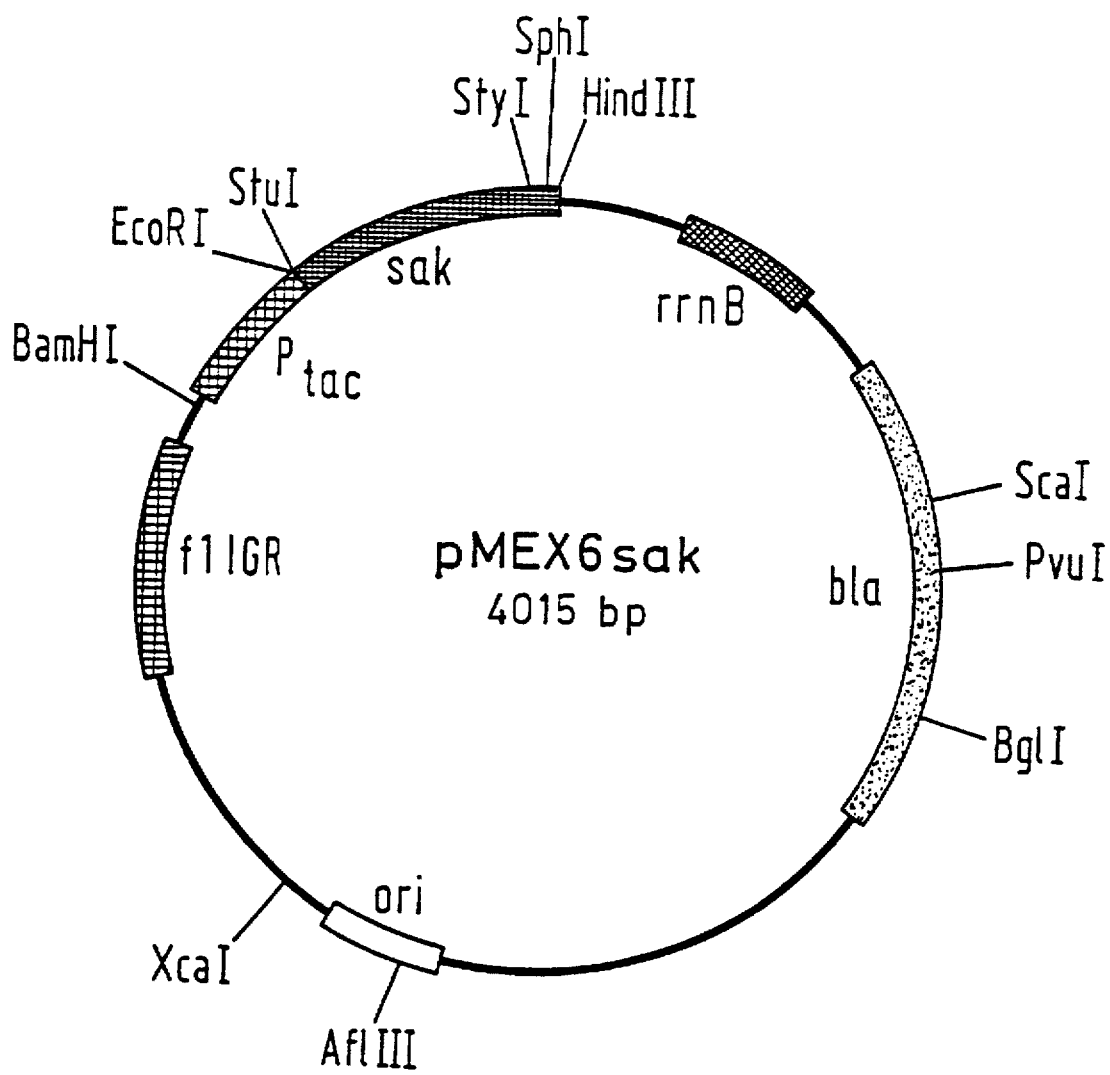
FIG. 3: Gene and restriction map of the plasmid family pMEX6sak.

The EcoRI/PstI fragment described above is isolated from the base plasmid pTZ19Rsak1 and subsequently inserted into the plasmids pMEX5 and pMEX6 treated with EcoRI and PstI. After transformation into the E. coli strain TG1, the strains E. coli TG1 (pMEX503sak) and E. coli TG1 (pMEX602sak) carrying the expression plasmids pMEX503sak and pMEX602sak form (FIG. 3). In both plasmids, the expression of the target polypeptide is effected by a similar arrangement of the expression signals which is characterized in that, in the R;tac;SD;-;rrnBT1T2 configuration, two RESs arranged in tandem orientation according to FIG. 15 are connected upstream from the sak42D gene to be expressed. The second RBS has already been introduced into the plasmid pTZ19Rsak0 by the linker pair L1/L2 used for the reconstitution of the 5'-end of the mature sak42 gene (see Table 1), just like the recognition sequences for the restrictases StuI and NdeI.

The strain E. coli TG1 (pMEX602sak) is preferably used for the fermentative production of mature SAK42D.

To generate the expression plasmids according to the invention for definedly N-terminally shortened staphylokinases, the method of linker adaption known per se is used in the version described below. The linkers used are each time built up in such a way that they reconstitute the recognition sequence of StuI at the 5'-end after the ligation to a DNA cleaved with StuI. Downstream from the Stu-I site there follows a transition sequence up to the ATG start codon to which the nucleotide sequence of the native sak42D gene deleted around the corresponding codons is connected up to the next-following unicalar restriction cleavage site in the sak42D gene.

The unicalar BstUI cleavage site in the sak42D gene is used for the construction of the expression plasmids for the SAK42D form shortened by 10 amino acids at the N-terminus, and the unicalar HaeIII cleavage site in the sak42D gene for the construction of the expression plasmids for the SAK42D form shortened by 14 amino acids at the N-terminus. According to the process, in both cases the semiphosphorylated linker pairs L5*/L6 (for ΔN10SAK42DΔ) and L7*/L8 (for ΔN14-SAK42D) are added first in tried and tested manner to the two ends of the expression plasmid pMEX602sak opened with StuI with the help of T4-DNA ligase. Through subsequent digestion with HindIII, the sak42D gene is completely removed from the linker-modified vectors in question. The thus-obtained linear expression vectors, now flanked by BstUI/HindIII or HaeIII/HindIII ends, are linked with the help of T4-DNA ligase to the BstUI/HindIII or HaeIII/HindIII fragment carrying the pertinent shortened sak42D gene (both fragments are isolated from pTZRsak1 after cleavage with the corresponding restrictase pairs).

After cloning in E. coli TG1, the respective strains E. coli TG1 (pMEX6N10sak) and E. coli TG1 (pMEX6N14sak) replicating the expression plasmids pMEX6N10sak and pMEX6N14sak are obtained according to the described procedure.

PART-STEP C
Construction of the base plasmids of the type pUC19sakM26X carrying the mature SAKM26Xs (with X=I, R, V, K, L, C, A, H, G and S)

Figure 2:
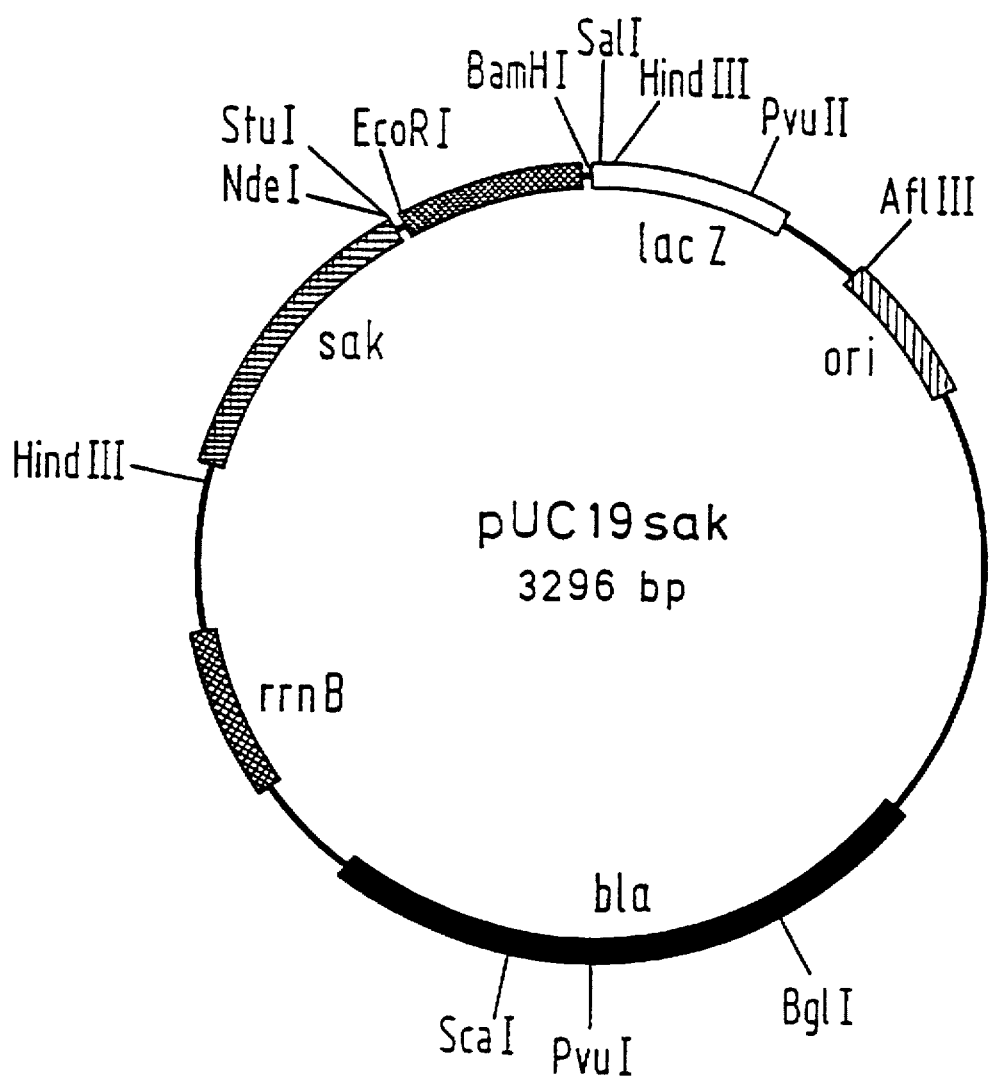
FIG. 2: Gene and restriction map of the plasmid family pUC19sak.

The construction by means of genetic engineering of the plasmid family of the type pUC19sakM26X (see also FIG. 2) is performed in three sub-steps, whereby in a first step (part-step C1), the coding sequence for amino acids 1 to 22 of SAK42D including translation connection sequences is built up first, in a second step (part-step 2) the sequence coding from amino acid 32 of SAK42D is built up and in a final third step (part-step C) the complete genes for the mature SAKM26Xs are built up using a range, listed in Table 1, of chemically synthesized oligonucleotide linkers.

PART-STEP C1

The construction of the coding sequence of amino acid positions 1 to 22 including the introduction of a portable translation signal sequence (RBS) and of transition sequences to the expression start codon ATG as well as an additional sequence to the final expression connection of the coding DNA sequence of SAKM26X to the translation signal sequence (from pMEX6) takes place through cloning of chemically synthesized oligonucleotide linkers with the corresponding nucleotide series in 2 stages via the intermediate plasmid pUC19sak0.

Firstly, the semiphosphorylated linker pair L9*/L10 are added on in a manner known per se by means of T4-DNA ligase to the two ends of the vector plasmid pUC19 linearized by EcoRI cleavage. The linker pair used is built up according to the process in such a way that, besides the portable nucleotide sequence for the translation connection, it contains the coding DNA sequence for the amino acids 1 to 3 and the first two nucleotides of amino acid 4 as well as the recognition sequence, not appearing on pUC19, of restrictase SfuI (overlaps codon 4) and a BamHI-compatible 5'-nucleotide end. The linker pair likewise added on at the polycloning sequence (PCS) is again split off through subsequent cleavage with BamHI. The formed-L9/L10-modified linear pUC19 vector is now circularized by means of T4-DNA ligase and then intermediately cloned. The plasmid pUC19sak0 forms.

In the succeeding process step, using a procedure which is identical in principle, the partially phosphorylated linker pair L11*/L12 (cf. Table 1) is added on to the plasmid pUC19sak0 opened via the introduced SfuI site. The sequence of codon 4 of the mature sakM26X gene is completed and the constantly coding nucleotide sequence for the amino acids 1 to 13 of the mature SAK products including the portable transition sequence is built up. Subsequent to this, the linker pair L11*/L12 added on to the PCS is split off again by cleavage with restrictase SphI. The previously kinased linker pair L13/L14* is now linked by means of T4-DNA ligase to the forming SphI end of the linear plasmid. In this way, the coding nucleotide sequence of amino acids 22 to 16 and a unique cleavage site for the restrictase NaeI, which overlaps the codon 22 and the SphI site, is introduced from the reconstituted SphI site in the reading direction to the overhanging 5'-end of the linker pair. The forming linear pUC19 derivative also carries at its ends a 6 nucleotides ling single-stranded DNA sequence complementary to each other which completes codons 14 and 15 after annealing.

After phosphorylation of the free overhanging 5'-nucleotide ends, the linker-modified vector fragment is circularized in the manner described. Through cloning, the plasmid pUC19sak1A is obtained which includes inter alia the unique cleavage site for NaeI with connection sequence to codon 23.

PART-STEP C2

The construction of the plasmid pUC19sakA2, which contains the DNA sequence coding for the C-terminus of SAKM26X from amino acid 32 onwards in a form adapted for the following process steps, takes place in 2 genetic engineering process steps which are matched to each other, using the intermediate plasmid pUC19sakA1 from part-step C1.

Plasmid pMET5 is again used to provide the DNA part-sequence needed according to the process which codes for the amino acids 44 to 124 of SAKM26X. To separate the 3'-flanking DNA section, in this case the 1.2 kb large SalI/PstI fragment is isolated from pMET5 first, and from this there is obtained in a favourable manner—as already described—by consecutive restrictase digestion with AvaI, AvaII and HinfI the 361 bp large SalI/HinfI fragment in which the last 27 bp of the sequence coding for SAK42D have likewise been removed.

In a parallel process step, the HinfI/PstI-adaptable linker pair L15/L16* (cf. Table 1) is added on in the manner described previously to the PstI-ends of the vector pUC19 digested with the same enzymes and then, after cleavage with SalI, the now-linear SalI/HinfI-compatible, L15/16-linker-modified cloning vector pUC19 is obtained. The added-on linker pair contains in prefabricated manner the restored coding sequence downstream from codon 125 of the mature sak42D gene and also, while retaining the amino acid series between the amino acids 129 and 130 (quiet mutation) of the mature SAK42D (i.e. at nucleotide position 391), an additional recognition sequence for the restrictase StyI.

In the previously described modified linear vector pUC19, the isolated 361 bp large SalI/HinfI fragment (from pMET5) is inserted by means of T4-DNA ligase and, after transformation, the intermediate plasmid pUC19sakA1 is obtained first, which contains the complete coding DNA sequence of the mature sak42D gene from codon 4 onwards.

The thus-produced intermediate plasmid is linearized in continuation of the genetic engineering process via the EcoRI cleavage site and modified, in accordance with the described principle, by the semi-phosphorylated linker pair L17*/L18. These linkers, complementary to each other, contain inter alia the coding part-sequence of codons 32 to 43 as well as the first two nucleotides of codon 44 of the mature target sequence for SAKM26X whereby, in the codons 32 and 33, 38 to 40 and also 42 and 43, by way of deviation from the identical gene section of the mature native sak42D gene, 9 quiet mutations are additionally introduced. As a result, there form with maintenance of the amino acid sequence of SAKM26X in this region according to the process additionally desired unique recognition sites for the restrictases SalI, SacI and SacII. After subsequent HindIII digestion of the linker-substituted plasmid, the linear L17/L18-HindIII-flanked vector pUC19 and the 414 bp large sak gene sub-fragment are isolated at the same time from the cleavage mixture. From the latter of these there forms through cleavage with the restrictase MnlI inter alia the 290 bp large MnlI/HindIII fragment, which is compatible on the 5'-side to the 3'-end of the linker pair L17/L18 and which includes the DNA sequence coding the C-terminus of SAKM26X from amino acid 46 onwards, which is truncated after the TAA stop codon.

The thus-obtained DNA fragments are recombined with each other in known manner by means of T4-DNA ligase. After transformation and selection, finally the second base plasmid pUC19sakA2 is obtained, which jointly with pUC19sakA1 acts as starting plasmid for the following genetic engineering process steps.

PART-STEP C3

The uniting of the N- and C-terminal gene sections described in part-steps C1 and C2 and intermediately cloned to produce the constantly mature sakM26X genes is carried out with the help of complementary adapter oligonucleotides which code for the still-missing DNA part-sequences which comprise the region between the amino acids 23 to 31.

According to the process, 2 series of adaptor pairs (cf. Table 1) are used which are characterized by the following common properties:

They have the same sequence length;
they are 5'-terminally adaptable to a NaeI- and 3'-terminally adaptable to a SalI restriction cleavage end and
they contain, for codon position 26, such nucleotide series as in each case correspond to 12 different codons.

It results from these features that the thus built-up adapter oligonucleotides, produced via automated oligonucleotide synthesis, represent a mixture of 12 different oligonucleotide sequences (AG) each time and consequently in every series a mixture of 12 different adapter pairs each time is created. The mixture of the nucleotides during the synthesis of the oligonucleotides is to be conceived in such a way that, through the adapter series AG1/AG2 11 and through the adapter series AG3/AG4, 6 different amino acids are encoded at position 26 and potentially, as a consequence, the incorporation of a total of 17 different codons for amino acid 26 is made possible.

In the course of the genetic engineering process, the above-described adapter pairs AG1/AG2* and AG3/AG4* respectively are coupled first in separate reaction steps in a manner known per se to the free ends forming after SalI cleavage of pUC19sakA2. The fragment mixtures, now respectively AG1/AG2-HindIII and AG3/AG4-HindIII-terminated, which include the coding sequence region from codon 24 of the mature genes are isolated by subsequent HindIII digestion. The fragment mixtures determined by the adapter type in question are finally cloned in the base plasmid vector pUC19sak1 opened with NaeI and HindIII. The clones obtained after transformation are preselected by double cleavage of the obtained plasmid DNA with EcoRI and HindIII onto sakM26X gene-carrying plasmids. After DNA sequence analysis of a representative number of preselected recombinant plasmids, the plasmids pUC19sakM26I, pUC19sakM26R, pUC19sakM26V, pUC19sakM26T, pUC19M26K and pUCsakM26L, which code for mature SAKM26I, SAKM26R, SAKM26V, SAKM26T, SAKM26K and SAKM26L, are selected from the clones obtained using the adapter pairs AG1/AG2. In the same way, the plasmids pUC19sakM26C, pUC19sakM26A, pUC19sakM26H, pUC19sakM26G and pUC19sakM26S, coding for SAKM26C, SAKM26A, SAKM26H, SAKM26G and SAKM26S, are identified and selected from the AG3/AG4 series.

PART-STEP D

Construction of the expression plasmids pMEX6sakM26X; obtaining of recombinant producer strains The commercially available plasmid pMEX6, in which as is known the expression is arranged by the synthetic tac promoter, is again used as expression vector. The EcoRI/PstI fragments are isolated from the previously described 11 plasmids of the family pUC19sakM26X which carry mature sakM26X genes, and these are subsequently inserted into the expression vector pMEX6 treated with EcoRI and PstI, and samples of the *E. coli* strain TG1 are transformed anew with the obtained recombinant DNA. There forms a series of expression strains *E. coli* TG1 (pMEX6sakM26X) which accommodate the relevant representatives of the plasmid family pMEXsakM26X. In all the plasmids of this family, the expression of the target polypeptide in question is effected by an arrangement of expression signals analogous to the previously described expression plasmids.

After the formed SAKM26X polypeptides have been checked in a primary screening—carried out by means of the methods described below—for the development of plasminogen activator activity, the strains *E. coli* TG1 (pMEX6sakM26L) and *E. coli* TG1 (pMEX6sakM26C) are selected as producer strains for the obtaining of SAKM26L and SAKM26C for the further process steps for the fermentation and enrichment of the target polypeptides. PART-STEP E Determination of the expression and of the activity of the plasminogen activators The transformed *E. coli* strains *E. coli* TG1 (pMEX602sak), *E. coli* TG1 (pMEX6ΔN10sak), *E. coli* TG1 (pMEX6ΔN14sak), *E. coli* TG1 (pMEX6sakM26L) and *E. coli* TG1 (pMEX6sakM26C) are cultivated submersely in a complex full medium or in a synthetic medium up to the middle or late log phase for the detection of the intracellular SAK formation. In this growth phase, the expression of the SAK polypeptides is induced by the addition of isopropyl thiogalactopyranoside (IPTG). After a further 1 to 6 hours, the cells are harvested by centrifugation and resuspended in a phosphate buffer containing phenyl methyl sulphonyl fluoride (PMSF). Crude cell extracts are produced from the cells by means of ultrasonic decomposition and high-speed centrifugation.

The plasminogen activator polypeptides inter alia SAK42D, SAKN10, SAKN14, SAKM26L and SAKM26C are purified up to electrophoretic homogeneity from the clear-centrifuged crude extracts in a two-stage column chromatographic purification process which comprises successive chromatographies using S-SEPHAROSE (agarose beads cross-linked for chromatography) fast flow (Pharmacia, Freiburg) and Hiload-Phenylsepharose (Pharmacia, Freiburg).

The concentration of the plasminogen activators in the crude extracts and in the chromatographic fractions are determined semi-quantitatively after SDS-PAGE by calculating the band intensities according to coomassie brilliant blue colouring or by an indirect route via the proteolytic activity of the protease plasmin released from plasminogen. Methodically, this detection takes place through determination of the size of the lysis areas on plasminogen-caseinagar plates (D. Behnke and D. Gerlach, Mol. Gen. Genet., 210 (1987), 528–534) and by calorimetric determination of the nitrophenolate released from the synthetic plasmin substrate Chromozym PL.

Dissociation constants of complexes comprising plasminogen and SAK42D or the SAK polypeptides according to the invention are also determined by an affinity chromatographic method which is novel in this connection.

Embodiments

The following embodiments are intended to illustrate, with reference to examples, the individual steps of the processes for the construction of the vectors, for the carrying out of the product syntheses and for the treatment regime. However, they do not include detailed data concerning the standardized individual genetic engineering procedures such as the obtaining of plasmid DNA, cleavage of DNA with restriction enzymes, isolation of DNA fragments from agarose gels (exclusively by the glass milk method with GENECLEAN® (refined powderized glass particles), Bio101, La Jolla), insertion of DNA fragments into vector plasmids, transformation of bacterial receptor strains with plasmid DNA and DNA sequence analysis. Such processes are described in detail in a series of publications (e.g. in "Molecular Cloning, a Laboratory Manual", T. Maniatis, E. R. Fritsch and J. Sambrook, Cold Spring Harbor Laboratory Press, 2nd Edition, 1989 or in "Recombinant DNA Methodology", J-A. R Dillon, A. Nasim and E. R. Nestman, John Wiley & Sons) and known to the specialist as state of the art.

All the oligonucleotides used according to the invention are produced by automated oligonucleotide synthesis (Model 380B DNA Synthesizer, Applied Biosystems, Weiterstadt) using the phosphoramidite method.

EXAMPLE 1

Production of pTZ19Rsak0

Plasmid DNA is isolated in a manner known per se from the strain *E. coli* TG1 (pMET5). An adequate quantity of PMET5 (5 to 10 μg) is incubated in 20 μl of the corresponding reaction buffer with 20 units of SalI (Boehringer, Mannheim) for 2 hours at 37° C. The reaction is stopped by phenol extraction and the DNA precipitated after triple ether extraction with ethanol (EtOH). The precipitate is absorbed in double-distilled water ($H_2O$). An aliquot (200 ng) of the linear plasmid DNA is mixed each time with the 50-fold molar excess of linker L1 and of the linker 2 phosphorylated in a manner known per se and the mixture is set to ligation conditions with 10-fold TM buffer (700 mM tris-HCl (pH 7.5), 60 mM $MgCl_2$). The formation of the double-stranded linker DNA is achieved by heating of the reaction mixture to 80° C. and subsequent slow cooling to room temperature (RT).

$\frac{1}{10}$ volume equivalents 100 mM dithiothreitol (DTT) (Serva, Heidelberg) and 10 mM adenosintriphosphate (ATP) (Boehringer) and 0.2 units T4-DNA ligase (Boehringer) are added in each case to the reaction mixture and incubated for 12 hours at 15° C. The DNA is precipitated from out of the reaction mixture by the addition of the 2.5-fold volume of EtOH. The precipitate is absorbed in 50 μl B-buffer (Boehringer) and incubated with 20 units of HindIII (Boehringer) for 2 hours at 37° C. Through agarose gel electrophoresis and subsequent electroelution, a 1.2 kb large fragment is isolated in a manner known per se and subjected to ligation with- the vector pTZ19R (USB, Bad Homburg) previously digested in accordance with standard instructions with HindIII restriction enzyme. The reaction is stopped by 10 minutes' heating to 70° C. Half of the reaction mixture is used for the transformation of competent cells of the strain E. coli TG1.

The selection on transformants takes place through addition of 5-bromo-4-chloro-3-indolyl-beta-D-galactoside (X-Gal, Boehringer) and isopropylthiogalactopyranoside (IPTG, Boehringer) to the agar and selection of white cell colonies. Plasmid-DNA is isolated from 10 white transformant clones by means of the mini preparation method according to standard protocol (plasmid miniprep) and, after restriction analysis, subjected to sequencing according to the Sanger process using SEQUENASE™ (modified T7 DNA polymerase) (USB). Among the analysed clones are found 8 which display the expected sequence of the restored sak42D gene. One of these plasmids is selected and receives the designation pTZ19Rsak0.

EXAMPLE 2

Construction of the Plasmid pTZ19Rsak1

To separate the 3'-flanking regions, not coding for SAK42D, contained on the plasmid pTZ19Rsak0, the DNA of this plasmid pTZ19Rsak0 is isolated in accordance with standard instructions and a 1.2 kb large fragment is obtained by restriction digestion with EcoRI and HindIII (Boehringer) and agarose gel electrophoresis. Some 2 μg of this fragment are treated in a manner known per se successively with the restriction enzymes AvaII and HinfI (all Boehringer), as a result of which the electrophoretic isolation of the target fragment is facilitated. The 388 bp large HindIII/Hinf-sak42D gene fragment forming besides very small cleavage fragments upon the reaction is thus isolated by electrophoresis in a 1.8% agarose gel in a favourable manner. An aliquot (200 ng) of the aqueous DNA solution is reacted each time with the 50-fold molar excess of the linker L3* phosphorylated in a manner known per se and of the linker L4 and set at the reaction with $\frac{1}{10}$ volume equivalents of 10-fold concentrated TM buffer. The formation of the double-stranded linker DNA is achieved by heating of the reaction mixture to 65° C. and subsequent slow cooling to room temperature (RT).

$\frac{1}{10}$ volume equivalents 100 MM DTT and 10 mM ATP plus 0.2 units T4-DNA ligase are added to the reaction mixture each time and incubated for 16 hours at 15° C. The DNA is precipitated from out of the reaction mixture by the addition of the 2.5-fold volume of EtOH. The thus-obtained precipitate is absorbed in 15 μl ligation buffer (Boehringer) and incubated with ca. 50 ng of the plasmid pTZ19R dissolved in water which was previously treated in a manner known per se with the restriction enzymes EcoRI and PstI (Boehringer). 0.2 units of T4 DNA ligase are added to this reaction mixture and incubation takes place for 16 hours at 15° C. Half of this mixture is used for the transformation of competent cells of the strain E. coli TG1 in accordance with standard instructions. The selection on transformants takes place—as described previously—by the addition of X-Gal and IPTG to the agar and through selection of white cell colonies.

Plasmid minipreps are produced in known manner from 10 white transformant clones and four of these plasmids are subjected to plasmid sequencing. Three of the thus-analysed clones display the expected coding sequence, flanked by EcoRI and PstI sites, for mature SAK42D. One of these plasmids is selected and receives the designation pTZ19Rsak1.

EXAMPLE 3

Production of PMEX503sak and PMEX602sak

The 433 bp large fragment, flanked by EcoRI and PstI, is isolated in known manner from the base plasmid pTZ19Rsak1 after electrophoresis of the reaction mixture at 1.6% agarose. Parallel to this, the vectors pMEX5 and pMEX6 (medac) are treated in accordance with standard instructions with the restriction enzymes EcoRI and PstI and the vector fragments isolated. 50 ng of the thus-pretreated vector plasmids are united each time with 50 ng of the above 433 bp fragment in ligation buffer (Boehringer) and incubated for 16 hours at 15° C. after the addition of 0.2 units T4-DNA ligase. The ampicillin-resistant colonies obtained after the transformation in cells of E. coli TG1 are tested for the expression of staphylokinase activity by transfer to a plasminogen-containing casein agar (see D. Behnke and D. Gerlach (1987), loc. cit.), which is additionally also provided with 200 μm IPTG.

The plasmid DNA of every 4 clones producing lysis areas on the casein test plates is obtained in known manner and the nucleotide sequence is established by plasmid sequencing according to the standard protocol. Without exception, the thus-analysed plasmids displayed the correct sequence of the mature sak42D gene insert and of the 5'-flanking translation-determining regions.

One of these plasmids from the pMEX5 series receives the designation pMEX503sak, and another plasmid derived from pMEX6 is designated pMEX602sak. The strain E. coli TG1 (pMEX602sak) transformed with the expression plasmid pMEX602sak is selected for the following process steps for the fermentation and enrichment of SAK42D as a producer strain.

EXAMPLE 4

Construction of the Plasmids pMEX6ΔN10sak and pMEX6ΔN14sak

To produce the expression plasmids for the shortened sak42D genes, 10 μg of the plasmid pMEX9602sak are incubated in 50 μl H-buffer (Boehringer, Mannheim) with every 80 units StuI (Boehringer) for 2 hours at 37° C. The linear vector DNA is isolated in known manner after agarose gel electrophoresis (AGE) at a 1% gel. In two separate reaction mixtures, 2 μg each time of the linear plasmid DNA are reacted each time with the 50-fold molar excess of the linker pairs L5*/L6 and L7*/L8, of which the identified linker has in each case been previously phosphorylated in accordance with standard instructions. The formation of the double-stranded (ds) linker DNA is achieved by heating the corresponding linker partners in TM buffer to 80° C. and subsequent slow cooling to RT (annealing).

1/10 volume equivalents 100 mM DTT and 10 mM ATP plus 0.2 units T4 DNA ligase are added each time to the reaction mixtures and incubated for 12 hours at 15° C. The pertinent L5/L6 or L7/L8-flanked linear plasmid DNA is precipitated out from the reaction mixtures by the addition of the 2.5-fold volume of EtOH. The precipitates are absorbed in 20 μl B-buffer (Boehringer) and incubated with 20 units HindIII (Boehringer) each for 2 hours at 37° C., as a result of which the whole gene coding for native mature SAK42D is in each case split off from the remaining part of the vector plasmids. The sak gene-free, linker-modified pMEX6 fragments are isolated in a 1% agarose gel (AG) by electrophoresis.

Parallel to this, the 450 bp large sak42D gene fragment is isolated first in a manner known per se from 50 μg of the plasmid pTZ19ak1 by double digestion with 50 units each of the restrictases EcoRI and HindIII (Boehringer) plus subsequent AGE. In, again parallel, reaction mixtures 50 μl each time of this sak42 fragment (ca. 800 ng) are set to reaction conditions by the addition of the pertinent 10-fold concentrated reaction buffer. In the one mixture, the fragment is digested with 10 units of BstUI (NEB) at 60° C. and in the second mixture with 10 units of HaeIII (Boehringer) at 37° C. for 2 hours. Through subsequent AGE in a 1.8% AG, the 370 bp large BstUI/HindIII fragment is separated and isolated in one case, and the 358 bp large HaeIII/HindIII fragment in the other case.

Some 10 μl (80 ng) each time of the fragments dissolved in water and containing the sak42D gene are united with 10 μl (50 ng) each of the previously produced, linker-modified vector DNA dissolved in water, set at ligation conditions with 10-fold ligation buffer and incubated with 3 units of T4 DNA ligase for 15 hours at 15° C.

In each case half of the volumes of these ligation mixtures are used in accordance with standard instructions for the transformation of competent cells of the strain E. coli TG1. Some 20 transformants each grown on ampicillin nutrient agar plates (Amp-NA) are tested for the expression of staphylokinase activity after transfer onto plasminogen-containing casein nutrient agar, which activity is to be recognized after 2 to 5 hours' incubation at 37° C. in the form of lysis areas around the recess holes of the cells. Plasmid DNA is isolated in known manner from 10 each of the clones giving positive results in this test.

Those plasmids which carry the expected StuI/HindIII inserts are pre-selected by means of restriction analysis using HindIII and StuI (Boehringer). Through subsequent plasmid sequencing of 4 each plasmid minipreps of the corresponding series, the nucleotide sequence of the pertinent plasmid inserts is established. Without exception, the thus-investigated 4 clones of both series contain the expected sak42d sequence inserts flanked by EcoRI and HindIII sites. The expression plasmid carrying the sak42D gene N-terminally shortened by 10 amino acids bears the designation pMEX6ΔN10sak, while the expression plasmid carrying the sak42D gene shortened by 14 amino acids receives the designation pMEXN14 sak. The respective strains E. coli TG1 (pMEX6ΔN10sak) and E. coli TG1 (pMEX6ΔN14sak) transformed in each case with these plasmids are used according to the invention as producer strains for SAKN10 and SAKN14 respectively.

EXAMPLE 5

Production of the pUC19sakA1

The vector pUC19 is isolated first in a manner known per se from the strain E. coli JM109 (pUC19) via ethidium bromide-CsCl-density gradient centrifugation, and provided for all subsequent genetic engineering process steps.

Some 2 μg pUC19 are incubated in 30 μl H-buffer with 10 units of EcoRI until the vector is completely linearized (ca. 1 hour). After the addition of $H_2O$ to 90 μl and 10 μl 1M tris-Hcl (pH 8.5), extraction is performed with 100 μl phenol which is water-saturated and stabilized with 0.5% 8-oxyquinoline (called simply phenol hereinafter) and the mixture is then centrifuged for 2 minutes at 15000 rpm. After the setting of the separated aqueous phase to ammonium acetate ($NH_4$ acetate) concentration of 2.5M, the EcoRI-cleaved vector is precipitated with EtOH, the precipitate washed twice with 70% EtOH and then dissolved in 20 μl $H_2O$.

Parallel to this, the quantity of the linker L9 which corresponds to a 50- to 80-fold molar excess of free EcoRI ends of the linear vector pUC19 (ca. 0.1 $A_{260}$ units linker of nucleotide length 30 to 40 per μg linear vector) is phosphorylated in 15 μl reaction volume in the presence of 2 mM ATP under kinase conditions at 37° C. PNK. After 20 minutes, the reaction is completely stopped by heating to 70° C. for 15 minutes and, after cooling of the mixture in the ice bath, the same molar quantity of the linker L10 is added. The formation of the ds linker pair L9*/L10 is achieved by annealing. 18 μl EcoRI-cleaved pUC19-DNA are added to the thus-produced linker pair L9*/L10 and set to DNA ligase conditions in a reaction volume of 100 μl with 10-fold concentrated T4-DNA ligase buffer and $H_2O$. After the addition of 5 units of T4-DNA ligase, incubation takes place overnight (o.n.) at 15° C. The linker-modified vector is precipitated with EtOH in the presence of $NH_4$—Ac, the precipitate is washed twice with 70% EtOH and absorbed in 50 μl H-buffer after drying. After the addition of 15 units of BamHI (Boehringer), incubation takes place for 2 hours at 37° C. The reaction mixture is divided up in a 1% agarose gel and the vector fragment is isolated from the potassium iodide gel solution by means of 5 μl glass milk.

Some 50 ng of the L9/L10-BamHI-flanked pUC19 vector are incubated with 0.5 units T4-DNA ligase in a final volume of 20 μl under ligase conditions for 2 hours at 15° C. and then transformed into competent cells of E. coli TG1 in accordance with standard instructions. After transformation, these are coated onto nutrient agar plates (Serva) which are supplemented with 80 mg anipicillin/ml agar, X-Gal and IPTG (X-Gal-Amp-NA). Plasmid DNA is isolated from 6 white clones by means of the mini-preparation method, tested for the presence of a unique SfuI site (Boehringer) by cleavage with the corresponding restrictase, and the correct insertion of the linkers confirmed by plasmid sequencing. One of the positive clones is selected for the isolation of the intermediate plasmid, now designated pUC19sak0.

In the manner described previously by way of example, ca. 10 μg pUC19sak0 are linearized in 100 μl H-buffer with 30 units of SfuI, the reaction mixture is extracted with phenol, the opened vector plasmid is precipitated with EtOH and the precipitate, washed with 70% EtOH, is dissolved in 30 μl H$_2$O. At the same time, 0.4 A$_{260}$ units of the oligonucleotide L11 are kinased for addition on to 4 μg with PNK and, after inactivation of the PNK, complemented with the same molar quantity of the linker L12 through the annealing reaction to the ds linker pair. 12 μl of the SfuI-cleaved vector plasmid are added to this, set at 100 μl ligation buffer and incubated with 5 units of T4-DNA ligase for 4 hours at 16° C. After EtOH precipitation and washing, the plasmid dissolved in 80 μl M-buffer (Boehringer) is cleaved with 20 units of SphI (Boehringer) at 37° C. in the polycloning sequence (PCS) of the pUC19 replicon. The L11/L12-modified and SphI-end-carrying plasmid fragment is purified by electrophoresis in a 1% agarose gel with subsequent fragment isolation.

Adopting the procedure described previously, the second linker pair, namely L13/L14*, are added on overnight to ca. 600 ng of the purified fragment in 70 μl reaction volume by means of 4 units of T4-DNA ligase, whereby in a preceding step ca. 0.05 A$_{260}$ units of L14 in 15 μl kinase buffer were phosphorylated before the annealing step with the same molar quantity of L13 by means of PNK at the 5'-end. The T4-DNA ligase is inactivated by 15 minutes' heating-of the ligation mixture to 65° C. For the kinasing of the free 5'-OH ends present after the two-sided linker addition (at the L12- and L13 strand ends), the temperature-controlled ligation mixture is set at 3 mM ATP and incubated with 2 units of PNK for 25 minutes at 37° C. The plasmid fragment, now 5'-L12*/L13*-flanked, is separated from the linker excess by AGE as described and isolated.

Some 30 ng of the thus-obtained vector DNA are circularized overnight in vitro in the final genetic engineering construction step via the L12- and L13-complementary hexanucleotide ends with 1 unit of T4-DNA ligase. The ligation mixture is transformed into competent cells of *E. coli* TG1 and ⅓ of the ligation mixture is coated onto Amp-NA plates. Plasmid minipreps are produced from 12 clones and these are tested for the presence of the unique NaeI restrictase cleavage site (Boehringer). One of the NaeI-positive clones is selected after DNA sequence analysis as donor for the base plasmid with the expected linker insert.

This plasmid receives the designation pUC19sakA1 (first base plasmid) and is provided for the following construction steps to preparatory scale.

EXAMPLE 6

Construction of the Intermediate Plasmid pUC19sakA2

Adopting the same method as was described in detail for the production of pUC19sak0, a L14*/L15-flanked pUC19 vector fragment is produced first, by the adding on of the linker pair L14*/L15 to the PstI-ends (PstI, Boehringer) of the linearized vector pUC19 and subsequent cleavage in the PCS with SalI.

To obtain the gene sequence coding for the region of the amino acids 5 to 124 of the native mature SAK42D, an adequate quantity of the 1.2 kb large SalI/PstI fragment carrying the desired gene sequence is isolated from the plasmid pMET5. To this end, ca. 50 μg pMET5 in 250 μl H-buffer are first digested with 200 units of SalI and, after complete cleavage, PstI is re-digested with the same activity. The SalI/PstI fragment is isolated from a 1.2% agarose gel.

For the separation of the 3'-flanking DNA region not coding for SAK42D, some 2 μg of this fragment are incubated simultaneously with in each case 15 units of AvaI, AvaII in 150 μl under M-buffer conditions according to the part-process described in Example 2 and HinfI (all enzymes Boehringer) digested. The 361 bp large SalI/Hinf-sak42D gene fragment forming besides very small cleavage fragments is thus isolated in a favourable manner after electrophoresis in a 1.8% agarose gel.

Some 50 ng of the obtained SalI/HinfI fragment are inserted in 30 ng of the modified pUC19 vector described in the preceding section and cloned in *E. coli* TG1. Screening for the presence of StyI restriction cleavage sites (StyI, Boehringer) in selected clones and DNA sequence analysis confirm the presence of the expected insert sequence in a representative number of plasmid minipreps. One of the thus-characterized clones is selected and used as source for the plasmid named pUC19sakA1.

Adopting the same genetic engineering process steps, the linker pair L16*/L17 is added on to the ends of the EcoRI-opened plasmid pUC19sakA1. After phenol extraction and EtOH precipitation, some 3 μg of the linker-substituted plasmid fragment are digested in 80 μl B-buffer with 15 units of HindIII and the cleavage mixture is electrophoretically divided up in a 1.6% AG. Both the L16/L17-HindIII-flanked DNA fragment, acting as vector fragment in the following part-step, and the sak gene-carrying 414 bp large shred are isolated from the gel.

Some 250 ng of the last-mentioned subfragment are re-digested in 50 μl NE2-buffer with 10 units of MnlI (NEB), with the result that the 290 bp large MnlI/HindIII fragment can be isolated from the reaction mixture after gel electrophoresis from a 1.8% AG. Some 25 ng of the thus-obtained DNA fragment coding for the region from amino acid 46 onwards of SAK42D are finally cloned in *E. coli* TG1 in 30 ng of the above-isolated vector fragment in accordance with standard procedures.

A representative number of plasmid minipreps are tested for the presence of the sought DNA sections through double digestion both with SalI and HindIII and with SacII (Boehringer) and HindIII under adapted conditions in each case. After DNA sequence analysis, one of the positive clones is selected for the isolation of the second base plasmid, now designated pUC19sakA2.

EXAMPLE 7

Production of the SAKM26X Coding Donor Plasmids pUC19sakM26X

With the help of the automated oligonucleotide synthesis, the adapter mixtures AG1, AG2, AG3 and AG4, which each time represent a mixture of 12 sequence variants, are prepared by simultaneous incorporation of 3 or 4 different nucleotide building blocks into the first two positions of the codon 26 of the mature SAK42D. In accordance with the previously described procedure, in a first step the adapter mixture AG2 and, in another mixture, the adapter mixture AG4 is kinased. The phosphorylated linker mixtures are united by annealing with the pertinently complementary adapter mixtures AG1 or AG3 to create double-stranded DNA fragments. After the coupling-on of the thus-obtained adapter pair mixtures to the SalI-ends of the base plasmid pUC19sakA2 opened in separate reaction steps with this enzyme, with subsequent HindIII digestion, the pertinent reaction mixtures are obtained from which, through gel electrophoretic separation, the AG1/AG2-determined fragment mixture is isolated in one case and the AG3/AG4-determined fragment mixture in the other case. These mixtures are in each case limited by a HindIII- and a blunt, thus NaeI-compatible, end.

In each case, 150 ng of every fragment mixture are recombined with 100 ng NaeI/HindIII-linearized first base plasmid pUC19sakA1 and cloned in *E. coli* TG1. A plurality of clones of both series are pre-selected by restrictase double cleavages of the plasmid minipreps with EcoRI and HindIII for the presence of 436 bp large DNA inserts. In an extensive programme of DNA sequence analysis using primer S26, the plasmids which carry the following codons at position 26 of the mature sakM26X gene:

ATA(Ile), AGA(Arg), GTA(Val), ACA(Thr), AAA(Lys) and CTA(Leu)

are finally found from the AG1/A2 series.

Starting from the AG3/AG4 series, plasmids which display the following codons at position 26 of the sakM26X gene:

TGC(Cys), GCC(Ala), CAC(His), GGC(Gly) and TCC(Ser)

were selected in the same way.

EXAMPLE 8

Production of the Expression Plasmids of the pMEX6sakM26X Family

Some 20 μg of the vector pMEX6 are cleaved with 100 units of EcoRI until linearization is complete and re-digested with 100 units of PstI under identical conditions. The thus-cleaved vector is separated off from the PCS fragment by electrophoresis in a 1% AG. From the 11 donor plasmids which code the different sak gene variants, in each case the 433 bp large EcoRI/PstI fragments which additionally carry the translation signal sequences (RBS and ATG start codon) at the 5'-end are isolated by gel electrophoresis, as described, from a 1.6% AG.

Some 50 ng of every one of these expression-adapted sak gene fragments are ligated each time in separate mixtures with ca. 20 ng of the EcoRI/PstI-linearized pMEX6 vector and cloned in *E. coli* TG1. From 10 ml each culture solution of the *E. coli* TG1 strains containing the expression plasmid in question, the corresponding plasmids are isolated according to the miniprep method and characterized by restriction analysis with EcoRI and PstI and also by sequence analysis of both strands. The plasmids carrying the expected sak gene sequence in each case are assigned to the plasmid type pMEX6sakM26X.

EXAMPLE 9

Figure 4A:
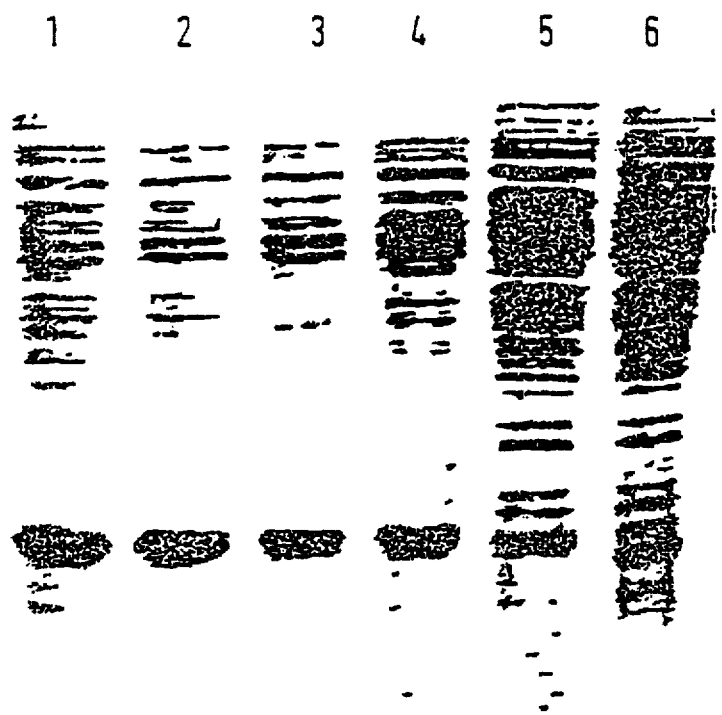
FIGS. 4A and 4B.
Figure 4B:
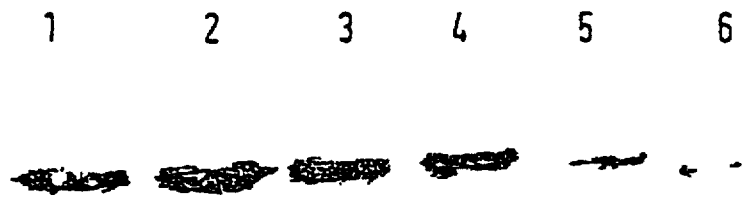

Qualitative Detection of the Superexpression of SAK42D and of the SAK Polypeptides According to the Invention For the analytical detection of the inducible superexpression of the SAK polypeptides according to the invention in the corresponding *E. coli* TG1 strains transformed with the plasmids pMEX602sak, pMEX6ΔN10sak, pMEX6ΔN14sak and pMEX6sakM26X, 5 ml in each case of a 2-fold concentrated trypton yeast extract medium which is additionally provided with 50 μg/ml ampicillin (2×TY-amp medium) are inoculated with 100 μl of an o.n. culture which has been prepared from a single colony of the pertinent recombinant *E. coli* TG1 producer strains. Cultivation is carried out for 3 hours at 37° C. accompanied by shaking and thereafter the expression is induced by the addition of a sterile ITPG solution (40 mg/ml isopropanol) up to a final concentration of 0.2 mM. The fermentation is continued for 4 hours and the cells of 1 ml culture medium are then collected by centrifugation. The cell pellet is suspended in 400 μl 40 mM phosphate buffer (pH 7.0), reacted with 100 μl 5-fold concentrated cell decomposition solution (20% SDS solution/mercaptoethanol/glycerol/0.02% bromophenol blue solution; 6:1:1:0.1; V/V) and decomposed for 5 minutes in the boiling water bath. Aliquots (2 to 6 μl ) of the thus-produced lysates are analysed according to standard protocol in a 1 mm thick 15% SDS polyacrylamide gel after Coomassie Brilliant Blue G250 colouring for the appearance of a band which contains superexpressed protein (FIG. 4). All the analysed crude lysates display the superexpression of the SAK polypeptide in question in the shape of a dominant protein band.

EXAMPLE 10

Fermentation of the *E. coli* TG1 Producer Strains and Purification of the SAK Polypeptides According to the Invention All strains are basically fermented and worked up in accordance with the following description.

The fermentation of the strains takes place at 37° C. in 500-ml round-bottomed flasks filled with 200 ml medium under intensive shaking without additional aeration. For this, 5 ml 2×TY amp medium are inoculated with a single colony of the corresponding strain and pre-cultivated for ca. 16 hours at 37° C. with shaking. 2 ml in each case of this pre-culture are used for the inoculation of 200 ml of the same medium. These cultures are shaken at 37° C., until an optical density of 0.4 to 0.9 A600 units is achieved. After this cell density has been reached, the expression of the staphylokinase genes coded on the expression plasmids is induced by the addition of 400 μl of a sterile aqueous IPTG solution (40 mg/ml). Thereafter, the cultures are shaken for a further 2 to 6 hours at 37° C. and then harvested by centrifugation at 4° C. and 4000 rpm. The cell precipitates are suspended in 1/20 to 1/40 volume equivalents (relative to the culture volume) decomposition buffer (40 mM phosphate buffer (pH 6.5), 30 mM NaCl, 10 mM EDTA, 10 mM EGTA and 10 mM β-mercaptoethanol) and reacted with phenyl methyl sulphonyl fluoride to a final concentration of 1 mM. The suspensions are cooled to 0° C. and decomposed at this temperature for 15 minutes with ultra-sound (output 100 to 120 watts).

The decompositions are stored at −20° C. until treatment. At the beginning of the purification, a maximum of 30 ml each time of decomposition suspension is thawed in the water bath (30° C.) and then centrifuged for 60 minutes at 4° C. and 25000 rpm. The supernatant liquids are diluted with H₂O to the 4-fold volume and then pumped onto a chromatography column equilibrated with 10 mM phosphate buffer (pH 6.5) and containing S-Sepharose fast flow (Pharmacia, Freiburg). The gel bed has a diameter of 2.6 cm and a height of 30 cm. The flow velocity upon deposition should not exceed 2 ml/min. Washing is then carried out with the equilibration buffer (flow velocity 3 to 4 ml/min.) until the base line of the UV detection (280 nm) is reached. The material passing the column unbound contains only traces of the target polypeptides and is discarded. The elution of the column (flow rate 3 to 4 ml/min.) takes place with 10 mm phosphate buffer (pH 6.5) which contains 250 mM NaCl. The elution profiles display several peaks, one of which contains the corresponding SAK polypeptide in enriched form (detection in SDS-PAGE). The corresponding peak fractions are united and then set at a final concentration of 2.0M NaCl through the addition of solid NaCl. In this way, the collected fractions are prepared directly for chromatography with phenyl sepharose. For this step, a ready-packed HiLoad phenyl sepharose HPXK 26/10 column (Pharmacia) is used which has been equilibrated with 10 mM phosphate buffer (pH 6.5) which contains 2.0M NaCl. After the trial deposition (flow rate 5.0 ml/min.), washing is carried out with equilibration buffer until the base line of the UV detection is reached (flow rate 12.6 ml/min.). The SAX forms are then eluted with a falling NaCl gradient (flow rate 12.6 ml/min.):

| 100% Buffer A —> | 25% Buffer A |
| 0% Buffer B —> | 75% Buffer B |

Buffer A: 10 mM phosphate buffer, pH 6.5; 2.0M NaCl
Buffer B: 10 mM phosphate buffer, pH 6.5

Figure 5:
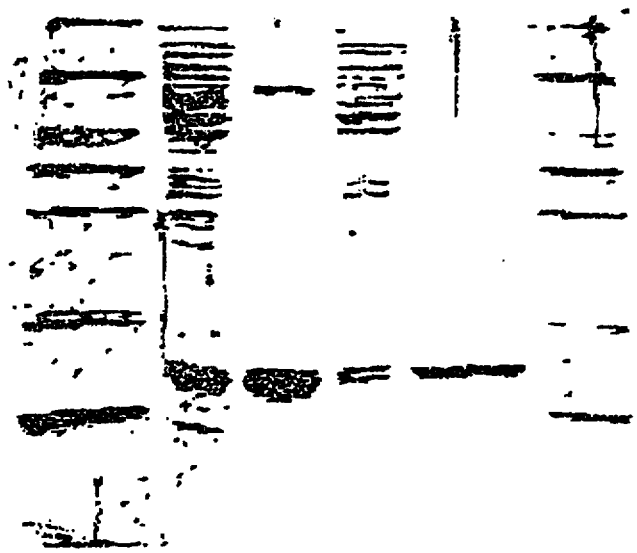
FIG. 5: Representation of the efficiency of the purification processes taking as an example the treatment of SAK42D.

The overall gradient volume on the present scale is 300 ml. The process allows pure SAK polypeptides (purity criteria SDS-PAGE and isoelectric focusing) to be obtained in only two purification steps. The effectiveness of the purification process can be seen in FIG. 5, in which the exemplary concentration of the target peptide SAKM26L from the crude cell extracts up to electrophoretic homogeneity is represented by means of a SDS gel.

EXAMPLE 11

Determination of the Specific Activity of the SAK Polypeptides According to the Invention The specific activity of a SAK form is defined as that quantity of plasmin (μmol) which is released per minute by 1 μmol of this SAK polypeptide from plasminogen (used in excess).

The protein content of the pertinent SAK polypeptide-containing parent solutions is established by means of the Bio-Rad Protein Assay (Bio-Rad, Munich) using bovine serum albumin as standard protein.

The determination of the plasmin release by the SAK polypeptides is carried out in two steps:

Firstly, dilution series (1 ng to 500 ng) of the SAK polypeptides are produced in 100 mM tris (pH 8.0). A reaction mixture, consisting of 30 μl plasminogen solution 20 mg plasminogen (Fluka), dissolved in 1 ml $H_2O$, 150 μl 100 mM tris buffer (pH 5.0) and 10 μl activator solution (dilution series SAK polypeptides) is then prepared. This mixture is incubated for 10 minutes at 25° C. (activation samples).

The plasmin substrate Chromozym-PL (Boehringer) is prepared as 2 mM solution in $H_2O$. 400 μl of 100 mM tris (pH 8.0) and 50 μl from the activation mixture are added to 50 μl of this solution. This mixture is incubated for 2 minutes at 25° C. The reaction is then stopped off with 25 μl concentrated acetic acid. Parallel to this, a plasmin calibration series is prepared, with 50 μl each of a plasmin dilution series with 400 μl 100 mM tris-buffer (pH 6.5) and 50 μl of the Chromozym-PL solution being incubated under the same conditions and stopped off. In reference samples (zero-value samples), the conversion of the plasmin substrate is prevented by the addition of 25 μl concentrated acetic acid in combination with the activation sample.

Reference samples, calibration samples and the actual measurement samples (each 250 μl) are pipetted into a microtitre plate with 96 cavities (flat bottom) and the adsorption at 405 nm is measured in a multi-channel photometer.

The quantity of plasmin which is released per minute by the SAK polypeptides contained in the starting solutions (dilution samples) can be calculated from the absorption values of the measured samples, taking into account the absorption values of the plasmin calibration series and of the reference samples.

Taking the protein content and the plasmin release into account, the specific activities of the SAK polypeptides can now be established and compared. In this way there result the specific activities summarized in Table 2 for the described staphylokinase forms.

TABLE 2

| SAK species | specific activity in μmol plasmin/(μmol SAK × min) | $K_D$ in mol/l |
| --- | --- | --- |
| SAK42D | 16.2 | $1.48 \times 10^6$ |
| SAKΔN10 | 22.7 | $2.21 \times 10^{-6}$ |
| SAKΔ14 | 8.1 | $4.40 \times 10^{-6}$ |
| SAKM26L | 36.6 | n.t. |
| SAKM26C | 21.1 | n.t. |

EXAMPLE 12

Determination of the Dissociation Constants of Staphylokinase Plasminogen Complexes by Means of Analytical Affinity Chromatography The principle of the method is that human plasminogen immobilized on a suitable carrier is introduced into a chromatography column and here enters into interaction with SAK polypeptide which is pumped over the column in specific quantities. The following relationship exists between the elution volume $V_E$ and the pertinent SAK concentration [SAK] in the sample:

$$1/(V_E - V_D) = K_D/M_{P_s} + [SAK]/M_{P_s}.$$

The variables have the following meanings:

| $V_D$ | dead volume of the column |
| --- | --- |
| $V_E$ | elution volume of the SAK polypeptides |
| $M_{P_s}$ | quantity of the interacting immobilized plasminogen in the column packing |
| [SAK] | concentration of the pertinent SAK polypeptide in the applied sample |
| $K_D$ | dissociation constant of the temporary complex comprising SAK form and plasminogen. |

The dependence of the reciprocal of the difference from column dead volume and elution volume of the SAK forms on the concentration of the SAK polypeptides in the given sample is linear over a specific concentration range. $M_{P_g}$ can be determined from the rise of the straight line, and thus the sought dissociation constant can be established by extrapolation to [SAK]=0.

Experimentally, the problem is solved in such a way that, firstly, plasminogen which has been isolated from human plasma in accordance with Deutsch und Mertz's instructions (D. G. DEUTSCH and E. T. MERTZ, Science, 170 (1970), 1095–1096) is coupled, using the Waters company's instructions, to Protein-Pak™ epoxy-activated (Waters). The degree of charging which is established is 5 mg protein per mg column matrix. A HR 5/5 chromatography column (Pharmacia), which is fitted with a cooling jacket and connected to a FPLC chromatography system (Pharmacia), is filled with the thus-charged affinity gel. All the described tests are carried out at 16° C. with a flow rate of 0.5 ml/min. using 0.1M tris-HCl (pH value 7.3).

After the conditioning of the column, the SAK samples are deposited in 25 μl volume zones each time onto the column, the quantity of protein contained in these volumes being varied between 0.5 g and 8 μg. The FPLC controller present in the system is used for the exact establishment of the pertinent maximum of the elution volume ($V_E$).

Using the described method, the dissociation constants represented in Table 2 are obtained for the interaction of plasminogen with selected SAK polypeptides.

EXAMPLE 13

Production of Monoclonal Anti-SAK-Antibody-Producing Hybridoma Clones

The immunization of female Balb/c/Han mice (age: 6–8 weeks) is carried out with highly pure, mature SAK42D, obtained using the process mentioned above from the recombinant producer *E. coli* TG1(pMEX602sak), the following immunization mode being observed:

- A first immunization dose of 50 μg of pure SAK42D is subcutaneously injected to every animal with complete Freund's adjuvant.

- Four weeks after this, a second dose, again of 50 μg pure SAK42D, is injected per animal with incomplete Freund's adjuvant.

- Three weeks later, a last dose, once more of 50 μg pure SAK42D, is injected intravenously to every animal without adjuvant.

(The preparations marketed by Fa. Difco are used as complete and incomplete Freund's adjuvant).

3 days after the intravenous SAK42D dose, the immunized animals are killed, and a cell suspension, mainly containing lymphocytes, is prepared from the spleens in a manner known per se (in HAT medium; ingredients are supplied by Fa. Serva). The fusion step with the myeloma cell line P3-X-63 Ag8-653 then takes place in standard manner. In detail, $10^7$ myeloma cells are coincubated with $5 \times 10^7$ spleen cells in a volume of 50 ml HAT medium.

For the subsequent separation of the formed cell hybrids from non-fused myeloma cells, the above cell suspension is distributed in 200 μl portions into the cavities (1 to 2 cells per cavity) of cell culture plates (96 cavities; Fa. Nunc). Under these conditions, incubation takes place for 3 weeks at 37° C. in an incubator with air moistening and 5% $CO_2$ addition. The following single-clone cultivation (duration 2 weeks; other conditions as above) is undertaken in HT medium (ingredients likewise from Serva). All the single-clone cultures are then cultivated further in RPMI standard medium (Serva) which contains 15% foetal calf serum (Flow). In this process stage, the testing of the individual hybridoma cell clones for a production of SAK-specific antibodies takes place with the help of a solid-phase ELISA. Micro-test plates in which SAK42D is bound to the surface of their cavities (5 μg/cavity; PBS buffer) is used in this assay. The blocking of the thus-pretreated cavities takes place with gelatin-containing (0.5% gelatin) PBS buffer which contains 0.05% Tween-20 (Serva). The hybridoma culture supernatant liquids to be tested are then poured into the cavities. The establishment of the binding of anti-SAK antibodies contained in the culture supernatant liquids takes place with an antibody conjugate which consists of goat-anti-mouse immunoglobulin antibodies labelled with peroxidase (medac).

In this way, 11 hybridoma clones are identified which are capable of the biosynthesis of anti-SAK antibodies. The cell clones are preserved and frozen in this stage.

The two hybridoma lines with the working designations alphaSAK IG8/H6 and alphaSAK IIA4/A10 pass in RPMI medium with 15% FCS additive (for suppliers, see above) through a recloning process (duration 14 days; 37° C.; incubator with air-moistening and 5% $CO_2$ addition). Thereafter, there is cumulatively obtained from each of the two clones (by continued cultivation in RPMI medium) a larger quantity of culture supernatant liquid (ca. 2 l) which in each case makes it possible to obtain the anti-SAK antibodies IG8/H6 and IIA4/A10 in pure form by affinity chromatography using immobilized SAK42D. To this end, recombinant SAK42D is coupled to CNBr-SEPHAROSE-4B (Pharmacia) (10 mg protein/ml SEPHAROSE). The corresponding hybridoma culture supernatant liquids are additionally reacted with NaCl (final concentration 0.5M) and Tween-20 (final concentration 0.05%; Serva) and then chromatographed over a column which contains the immobilized SAK42D. The column-washing is carried out with PBS buffer which additionally contains 0.5M NaCl. The elution of the bound anti-SAK antibodies is carried out with 0.5M NaCl; 0.2M glycine; pH 2.8. The protein-containing eluate fractions are immediately neutralized with NaOH.

The purified antibodies are henceforth ready to be used for the stated purposes (cf. Examples 14 to 18).

EXAMPLE 14

Use of the Monoclonal Anti-SAK Antibody IIA4/A10 for Western Blot Tests

SAK42D-containing protein samples (e.g. crude lysates) are electrophoretically separated in SDS polyacrylamide gels and then transferred onto nitrocellulose in a manner known per se. Through a temporary protein colouring by means of Ponceau-S (Serva), the position of the protein bands on the nitrocellulose receiver layer is made visible, assigned to specific molecular weight markers and labelled where appropriate. The nitrocellulose blot is then blocked with washing buffer (0.5M NaCl, PBS, 0.05% Tween 20; Serva) which contained 5% skimmed milk powder (ca. 2 hours at room temperature).

In the next step, the treatment with the antibody IIA4/A10, which is diluted 1000-fold in the washing buffer (contained 1% skimmed milk powder), takes place. The nitrocellulose blot is then treated with a goat-anti-mouse immunoglobulin antibody POD conjugate (medac) (dilution 1000-fold in washing buffer with 1% skimmed milk powder). The "development" of the Western Blot takes place with diaminobenzidine in the presence of hydrogen peroxide. Only SAK42D bands and those of other SAK polypeptides are coloured on the nitro-cellulose receiver layer (FIG. 4). The process can be used for the identification of the native SAK42D and for epitope characterization including staphylokinase polypeptides.

EXAMPLE 15

ELISA Test System for the Quantitative Detection of Staphylokinase

Microtitration plates are firstly coated with a polyclonal pig anti-SAK antibody which was purified by means of affinity chromatography (2 μg/cavity).

The said antibodies are obtained by firstly immunizing a pig three times with 500 μg pure SAK42D each time. The hyperimmune serum then obtained is purified at immobilized SAK42D (analogous to the process described in Example 13). The duration of the coating procedure is 15 hours at 4° C. or 2 hours at 37° C. Treatment is then as described in Example 13 with gelatin-containing PBS buffer in order to block the plastic surface.

Figure 6:
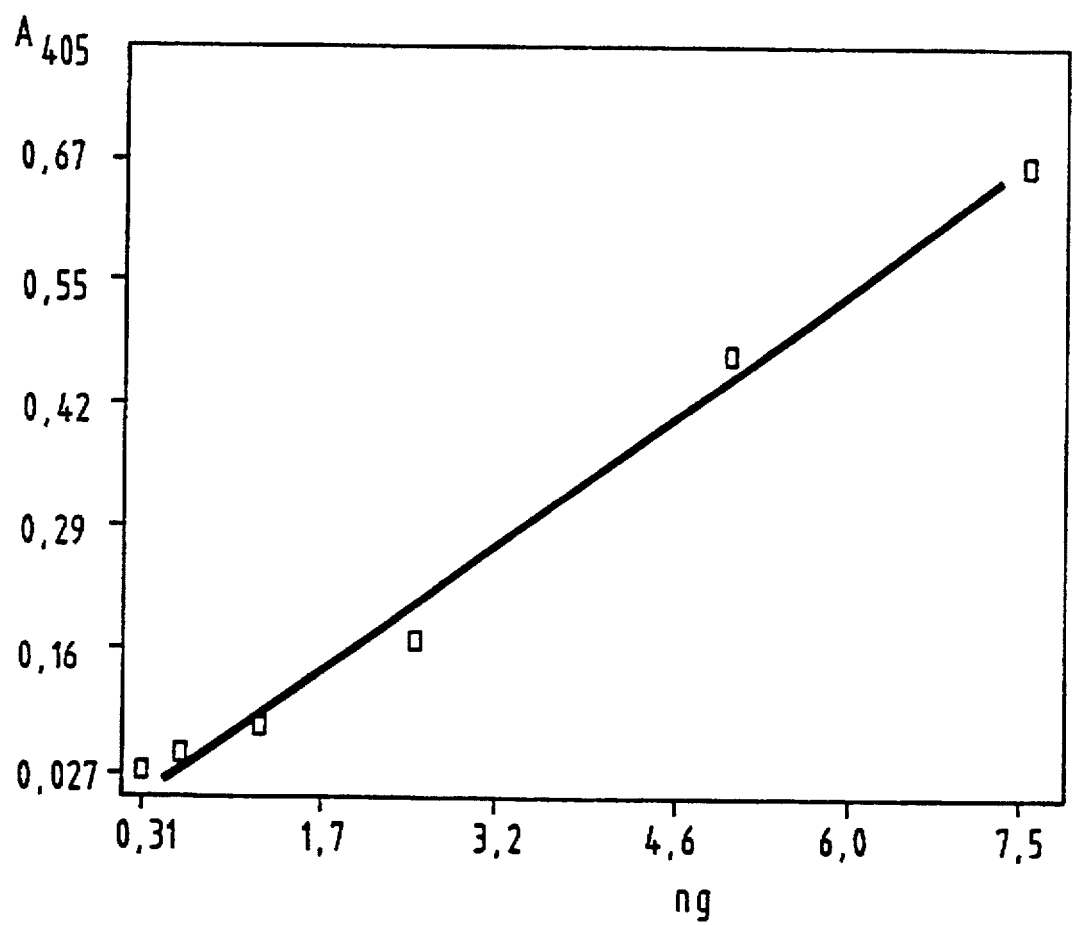
FIG. 6: Calibration curve of the ELISA test for the quantitative detection of the staphylokinase polypeptide SAK42D.

A standard dilution series comprising pure SAK42D in gelatin-containing PBS buffer is then produced. At the same time, the working dilutions of the samples to be tested are prepared. Standard series and working dilutions are poured into the cavities and incubated for 60 minutes at 37° C. After a washing procedure, the peroxidase-conjugated anti-SAK antibody IG8/H6 is poured into the cavities of the test plate in 1000-fold dilution (dilution medium is gelatin-containing PBS buffer). The quantitative evaluation of the test takes place calorimetrically at a wavelength of 492 nm using the substrate $H_2O_2$ and orthophenylene diamine. The calibration curve obtained in so doing passes linearly over a concentration range from 300 pg/ml to 7.5 ng/ml SAK (cf. FIG. 6).

The test permits quantitative SAK determination in bacterial decompositions, in the accompanying analysis upon SAK purification and in human serum.

EXAMPLE 16

Use of the Monoclonal Antibody IG8/ H6 for the Immune Precipitation of SAK Polypeptides The technique of immune precipitation is used for the identification of radioactively labelled SAK polypeptides, synthesized in vivo and in vitro, in cell lysates.

Figure 7:
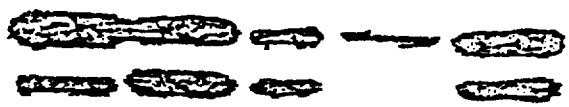
FIG. 7: Evaluation of an immune-precipitation reaction using mAB IG8/H6.

The cell lysate to be tested is mixed with a SDS solution and boiled (final concentration of the SDS 1%) and then diluted 10-fold with SDS tris-buffer (0.9% NaCl, 1% Triton X-100, 0.5% sodium desoxycholate, 0.1M tris-HCl; pH 8.2). 1 μl of the antibody IG8/H6 (suspension of an ammonium sulphate precipitate [50% saturation]) is added to this mixture and incubated overnight at 4° C. To precipitate the antigen-antibody complex, 10 mg protein A-SEPHAROSE-CL-4B (Pharmacia), pre-swollen in 100 μl STD-tris buffer, are added and shaken for 60 minutes at room temperature. The mixture is then centrifuged, the supernatant liquid discarded and the pellet washed 3 times, in each case with 5700 μl STD-tris buffer. After the washing, the pellet is absorbed in 40 μl SDS-PAGE sample buffer, boiled and deposited on a SDS polyacrylamide gel. The evaluation takes place autoradiographically. The result of an immune precipitation mixture is represented in FIG. 7.

EXAMPLE 17

Detection of the Activity of the mABs IG8/H6 and IIA4/A10 Inhibiting the Plasminogen-Activating Capacity of SAK Polypeptides Undiluted culture supernatant liquids of the two hybridoma clones (25 μl each) are mixed with 25 μl each of a diluted SAt42D sample (concentration: 20 ng protein/25 μl) in phosphate buffer (10 mM pH 6.5) (test formulation). Used as controls are formulations to which, instead of SAK42D, the above phosphate buffer or streptokinase (kabikinase, kabivitrum) diluted in phosphate buffer is added (control formulations). These formulations are incubated for 30 minutes at room temperature. 10 μl each are then removed from the test and control formulations and introduced into another test formulation which allows the measurement of the plasmin release induced by a SAK polypeptide according to the invention, preferably by SAK42D (test carried out in a micro-testplate with 96 cavities). To this end, the aforementioned 10 μl aliquots are reacted with 30 μl of a plasminogen solution (20 mg/ml plasminogen [Behring], dissolved in $H_2O$) and 150 μl tris-buffer (100 mM tris, pH 8.0) and incubated for 10 minutes at 25° C.

50 μl each are then removed and added to another formulation, consisting of 400 μl tris-buffer (100 mM tris, pH 8.0) and 50 μl plasmin substrate CHROMOZYM-PL (Boehringer; 2 mM solution in $H_2O$) and incubated for 2 minutes at 25° C. The reaction is stopped with 25 μl each concentrated acetic acid. The absorption measured at a wavelength of 405 nm is in direct proportion to the plasmin release originally induced by SAK42D. An activity of the antibodies inhibiting the action of SAK polypeptides is expressed in reduced absorption values and thus in a reduced plasmin release.

In the case of the monoclonal antibodies IG8/H6 and IIA4/A10, this effect is clearly detectable: in the given test arrangement the antibodies IG8/H6 and IIA4/A10 inhibit the release of plasmin 18.8- and 17.5-fold respectively.

EXAMPLE 18

Use of the mAB IG8/H6 for the Immune Affinity Chromatographic Purification of Staphylokinase The process consists of two part-steps. In the first step (1), the mAB IG8/H6 is mobilized at a chromatographable carrier. The second step (2) comprises the direct chromatographic obtaining of native SAK42D or of SAK polypeptides e.g. from bacterial crude extracts.

(1) The mAB IG8/H6 purified by means of affinity chromatography (total quantity 20 mg) is firstly dialysed against coupling buffer (0.5M NaCl, 0.1M $NaHCO_3$; pH 8.3). The coupling takes place with CNBr-SEPHAROSE-CL-4B (Pharmacia). A corresponding quantity of this SEPHAROSE (0.7 g) is pre-swollen in 1 mM HCl. The coupling of the mAB itself takes place in coupling buffer (2 hours at room temperature with occasional careful stirring and then overnight). The supernatant liquid is then removed and the SEPHAROSE washed several times with coupling buffer.

The SEPHAROSE charged with mAB IG8/H6 is then treated with 1M ethanolamine (pH 8.0) (2 hours at room temperature). Joined to this step are washings with 0.1M borate buffer, which contains 0.5M NaCl (pH 8.0), and 0.1M acetate buffer, which contains 0.5M NaCl (pH 4.0). The washings are carried out 5 times each with borate buffer and acetate buffer alternating. At the end, washing is carried out with 0.2M glycine/ HCl buffer (pH 2.8), which contains 0.5M NaCl, and the Sepharose is then transferred into PBS buffer.

(2) The SEPHAROSE charged with mAB IG8/H6 is transferred into a chromatography column (diameter 1 cm) and washed (at least 20 column volumes) with PBS buffer which contained 0.05 % Tween-20 and additionally 0.5 M NaCl . The SAK-containing bacterial decompositions produced in 4-fold concentrated PBS buffer with the addition of protease inhibiting substances are brought, by dilution with distilled water and with the addition of NaCl and Tween-20, into a buffer composition which corresponds to the column wash buffer. There follows the charging of the affinity column with this material. Washing is then carried out (at least 20 column volumes) with PBS buffer which contains 0.5M NaCl (but no Tween-20) until no more protein is eluted from the column (UV detector; wavelength 280 nm). The elution of the column takes place with 0.2M glycine/HCl buffer (pH 2.8) which contains 0.5M NaCl. The protein-containing eluate fractions are neutralized immediately, just like the column matrix.

SAK42D or the SAK polypeptides are present in the column eluate in electrophoretically pure form.

SEQUENCE LISTING ( 1 ) GENERAL INFORMATION:

( i i i ) NUMBER OF SEQUENCES: 40

( 2 ) INFORMATION FOR SEQ ID NO: 1:

( i ) SEQUENCE CHARACTERISTICS:
        ( A ) LENGTH: 414 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "recombinant DNA"

( v i ) ORIGINAL SOURCE:
        ( A ) ORGANISM: Staphylococcus aureus
        ( B ) STRAIN: Phage 42D ( i x ) FEATURE:
        ( A ) NAME/KEY: CDS
        ( B ) LOCATION: 1..414

( i x ) FEATURE:
        ( A ) NAME/KEY: -
        ( B ) LOCATION: 1..3
        ( D ) OTHER INFORMATION: /note= "start codon"

( i x ) FEATURE:
        ( A ) NAME/KEY: -
        ( B ) LOCATION: 412..414
        ( D ) OTHER INFORMATION: /note= "stop codon"

( i x ) FEATURE:
        ( A ) NAME/KEY: mat_peptide
        ( B ) LOCATION: 4..411
        ( D ) OTHER INFORMATION: /product="mature protein"

( x i ) SEQUENCE DESCRIPTION: SEQ ID NO: 1:

```
ATG TCA AGT TCA TTC GAC AAA GGA AAA TAT AAA AAA GGC GAT GAC GCG      48
Met Ser Ser Ser Phe Asp Lys Gly Lys Tyr Lys Lys Gly Asp Asp Ala
 -1   1           5                  10                  15

AGT TAT TTT GAA CCA ACA GGC CCG TAT TTG ATG GTA AAT GTG ACT GGA      96
Ser Tyr Phe Glu Pro Thr Gly Pro Tyr Leu Met Val Asn Val Thr Gly
                  20                  25                  30

GTT GAT GGT AAA AGA AAT GAA TTG CTA TCC CCT CGT TAT GTC GAG TTT     144
Val Asp Gly Lys Arg Asn Glu Leu Leu Ser Pro Arg Tyr Val Glu Phe
             35                  40                  45

CCT ATT AAA CCT GGG ACT ACA CTT ACA AAA GAA AAA ATT GAA TAC TAT     192
Pro Ile Lys Pro Gly Thr Thr Leu Thr Lys Glu Lys Ile Glu Tyr Tyr
         50                  55                  60

GTC GAA TGG GCA TTA GAT GCG ACA GCA TAT AAA GAG TTT AGA GTA GTT     240
Val Glu Trp Ala Leu Asp Ala Thr Ala Tyr Lys Glu Phe Arg Val Val
     65                  70                  75

GAA TTA GAT CCA AGC GCA AAG ATC GAA GTC ACT TAT TAT GAT AAG AAT     288
Glu Leu Asp Pro Ser Ala Lys Ile Glu Val Thr Tyr Tyr Asp Lys Asn
 80                  85                  90                  95

AAG AAA AAA GAA GAA ACG AAG TCT TTC CCT ATA ACA GAA AAA GGT TTT     336
```

```
        Lys  Lys  Lys  Glu  Glu  Thr  Lys  Ser  Phe  Pro  Ile  Thr  Glu  Lys  Gly  Phe
                       100                      105                      110

GTT  GTC  CCA  GAT  TTA  TCA  GAG  CAT  ATT  AAA  AAC  CCT  GGA  TTC  AAC  TTA                   384
Val  Val  Pro  Asp  Leu  Ser  Glu  His  Ile  Lys  Asn  Pro  Gly  Phe  Asn  Leu
               115                      120                      125

ATT  ACM  AAG  GTT  GTT  ATA  GAA  AAG  AAA  TAA                                                 414
Ile  Thr  Lys  Val  Val  Ile  Glu  Lys  Lys   *
          130                      135
```

( 2 ) INFORMATION FOR SEQ ID NO: 2:

( i ) SEQUENCE CHARACTERISTICS:
        ( A ) LENGTH: 137 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 2:

```
          Met  Ser  Ser  Ser  Phe  Asp  Lys  Gly  Lys  Tyr  Lys  Lys  Gly  Asp  Asp  Ala
          - 1    1                  5                     10                      15

Ser  Tyr  Phe  Glu  Pro  Thr  Gly  Pro  Tyr  Leu  Met  Val  Asn  Val  Thr  Gly
                         20                      25                      30

Val  Asp  Gly  Lys  Arg  Asn  Glu  Leu  Leu  Ser  Pro  Arg  Tyr  Val  Glu  Phe
                         35                      40                      45

Pro  Ile  Lys  Pro  Gly  Thr  Thr  Leu  Thr  Lys  Glu  Lys  Ile  Glu  Tyr  Tyr
                    50                      55                      60

Val  Glu  Trp  Ala  Leu  Asp  Ala  Thr  Ala  Tyr  Lys  Glu  Phe  Arg  Val  Val
                    65                      70                      75

Glu  Leu  Asp  Pro  Ser  Ala  Lys  Ile  Glu  Val  Thr  Tyr  Tyr  Asp  Lys  Asn
          80                      85                      90                      95

Lys  Lys  Lys  Glu  Glu  Thr  Lys  Ser  Phe  Pro  Ile  Thr  Glu  Lys  Gly  Phe
                         100                     105                      110

Val  Val  Pro  Asp  Leu  Ser  Glu  His  Ile  Lys  Asn  Pro  Gly  Phe  Asn  Leu
                         115                     120                      125

Ile  Thr  Lys  Val  Val  Ile  Glu  Lys  Lys
                    130                     135
```

( 2 ) INFORMATION FOR SEQ ID NO: 3:

( i ) SEQUENCE CHARACTERISTICS:
        ( A ) LENGTH: 414 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "recombinant DNA"

( v i ) ORIGINAL SOURCE:
        ( A ) ORGANISM: Staphylococcus aureus
        ( B ) STRAIN: Phage PhiC ( i x ) FEATURE:
        ( A ) NAME/KEY: CDS
        ( B ) LOCATION:1..414

( i x ) FEATURE:
        ( A ) NAME/KEY: -
        ( B ) LOCATION:1..3
        ( D ) OTHER INFORMATION:/note= "start codon"

( i x ) FEATURE:
        ( A ) NAME/KEY: -
        ( B ) LOCATION:412..414
        ( D ) OTHER INFORMATION:/note= "stop codon"

( i x ) FEATURE:
    ( A ) NAME/KEY: mat_peptide
    ( B ) LOCATION: 4..411
    ( D ) OTHER INFORMATION:/product="mature protein"

( x i ) SEQUENCE DESCRIPTION: SEQ ID NO: 3:

```
ATG  TCA  AGT  TCA  TTC  GAC  AAA  GGA  AAA  TAT  AAA  AAG  GGC  GAT  GAC  GCG      48
Met  Ser  Ser  Ser  Phe  Asp  Lys  Gly  Lys  Tyr  Lys  Lys  Gly  Asp  Asp  Ala
 -1    1              5                        10                        15

AGT  TAT  TTT  GAA  CCA  ACA  GGC  CCG  TAT  TTG  ATG  GTA  AAT  GTG  ACT  GGA      96
Ser  Tyr  Phe  Glu  Pro  Thr  Gly  Pro  Tyr  Leu  Met  Val  Asn  Val  Thr  Gly
                    20                        25                        30

GTT  GAT  GGT  AAA  GGA  AAT  GAA  TTG  CTA  TCC  CCT  CAT  TAT  GTC  GAG  TTT     144
Val  Asp  Gly  Lys  Gly  Asn  Glu  Leu  Leu  Ser  Pro  His  Tyr  Val  Glu  Phe
               35                        40                        45

CCT  ATT  AAA  CCT  GGG  ACT  ACA  CTT  ACA  AAA  GAA  AAA  ATT  GAA  TAC  TAT     192
Pro  Ile  Lys  Pro  Gly  Thr  Thr  Leu  Thr  Lys  Glu  Lys  Ile  Glu  Tyr  Tyr
          50                        55                        60

GTC  GAA  TGG  GCA  TTA  GAT  GCG  ACA  GCA  TAT  AAA  GAG  TTT  AGA  GTA  GTT     240
Val  Glu  Trp  Ala  Leu  Asp  Ala  Thr  Ala  Tyr  Lys  Glu  Phe  Arg  Val  Val
     65                        70                        75

GAA  TTA  GAT  CCA  AGC  GCA  AAG  ATC  GAA  GTC  ACT  TAT  TAT  GAT  AAG  AAT     288
Glu  Leu  Asp  Pro  Ser  Ala  Lys  Ile  Glu  Val  Thr  Tyr  Tyr  Asp  Lys  Asn
 80                        85                        90                        95

AAG  AAA  AAA  GAA  GAA  ACG  AAG  TCT  TTC  CCT  ATA  ACA  GAA  AAA  GGT  TTT     336
Lys  Lys  Lys  Glu  Glu  Thr  Lys  Ser  Phe  Pro  Ile  Thr  Glu  Lys  Gly  Phe
                    100                       105                       110

GTT  GTC  CCA  GAT  TTA  TCA  GAG  CAT  ATT  AAA  AAC  CCT  GGA  TTC  AAC  TTA     384
Val  Val  Pro  Asp  Leu  Ser  Glu  His  Ile  Lys  Asn  Pro  Gly  Phe  Asn  Leu
               115                       120                       125

ATT  ACA  AAG  GTT  GTT  ATA  GAA  AAG  AAA  TAA                                   414
Ile  Thr  Lys  Val  Val  Ile  Glu  Lys  Lys   *
          130                       135
```

( 2 ) INFORMATION FOR SEQ ID NO: 4:

( i ) SEQUENCE CHARACTERISTICS:
        ( A ) LENGTH: 137 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 4:

```
Met  Ser  Ser  Ser  Phe  Asp  Lys  Gly  Lys  Tyr  Lys  Lys  Gly  Asp  Asp  Ala
 -1    1              5                        10                        15

Ser  Tyr  Phe  Glu  Pro  Thr  Gly  Pro  Tyr  Leu  Met  Val  Asn  Val  Thr  Gly
                    20                        25                        30

Val  Asp  Gly  Lys  Gly  Asn  Glu  Leu  Leu  Ser  Pro  His  Tyr  Val  Glu  Phe
               35                        40                        45

Pro  Ile  Lys  Pro  Gly  Thr  Thr  Leu  Thr  Lys  Glu  Lys  Ile  Glu  Tyr  Tyr
          50                        55                        60

Val  Glu  Trp  Ala  Leu  Asp  Ala  Thr  Ala  Tyr  Lys  Glu  Phe  Arg  Val  Val
     65                        70                        75

Glu  Leu  Asp  Pro  Ser  Ala  Lys  Ile  Glu  Val  Thr  Tyr  Tyr  Asp  Lys  Asn
 80                        85                        90                        95

Lys  Lys  Lys  Glu  Glu  Thr  Lys  Ser  Phe  Pro  Ile  Thr  Glu  Lys  Gly  Phe
                    100                       105                       110

Val  Val  Pro  Asp  Leu  Ser  Glu  His  Ile  Lys  Asn  Pro  Gly  Phe  Asn  Leu
               115                       120                       125

Ile  Thr  Lys  Val  Val  Ile  Glu  Lys  Lys
```

( 2 ) INFORMATION FOR SEQ ID NO: 5:

( i ) SEQUENCE CHARACTERISTICS:
        ( A ) LENGTH: 414 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "recombinant DNA"

( v i ) ORIGINAL SOURCE:
        ( A ) ORGANISM: Staphylococcus aureus
        ( B ) STRAIN: strain 23, genomic DNA ( i x ) FEATURE:
        ( A ) NAME/KEY: -
        ( B ) LOCATION:1..3
        ( D ) OTHER INFORMATION:/note= "start codon"

( i x ) FEATURE:
        ( A ) NAME/KEY: CDS
        ( B ) LOCATION:1..414

( i x ) FEATURE:
        ( A ) NAME/KEY: -
        ( B ) LOCATION:412..414
        ( D ) OTHER INFORMATION:/note= "stop codon"

( i x ) FEATURE:
        ( A ) NAME/KEY: mat_peptide
        ( B ) LOCATION:4..411
        ( D ) OTHER INFORMATION:/product="mature protein"

( x i ) SEQUENCE DESCRIPTION: SEQ ID NO: 5:

```
ATG  TCA  AGT  TCA  TTC  GAC  AAA  GGA  AAA  TAT  AAA  AAA  GGC  GAT  GAC  GCG      48
Met  Ser  Ser  Ser  Phe  Asp  Lys  Gly  Lys  Tyr  Lys  Lys  Gly  Asp  Asp  Ala
 -1   1              5                        10                       15

AGT  TAT  TTT  GAA  CCA  ACA  GGC  CCG  TAT  TTG  ATG  GTA  AAT  GTG  ACT  GGA      96
Ser  Tyr  Phe  Glu  Pro  Thr  Gly  Pro  Tyr  Leu  Met  Val  Asn  Val  Thr  Gly
                     20                        25                       30

GTT  GAT  AGT  AAA  GGA  AAT  GAA  TTG  CTA  TCC  CCT  CAT  TAT  GTC  GAG  TTT     144
Val  Asp  Ser  Lys  Gly  Asn  Glu  Leu  Leu  Ser  Pro  His  Tyr  Val  Glu  Phe
                35                        40                       45

CCT  ATT  AAA  CCT  GGG  ACT  ACA  CTT  ACA  AAA  GAA  AAA  ATT  GAA  TAC  TAT     192
Pro  Ile  Lys  Pro  Gly  Thr  Thr  Leu  Thr  Lys  Glu  Lys  Ile  Glu  Tyr  Tyr
           50                        55                       60

GTC  GAA  TGG  GCA  TTA  GAT  GCG  ACA  GCA  TAT  AAA  GAG  TTT  AGA  GTA  GTT     240
Val  Glu  Trp  Ala  Leu  Asp  Ala  Thr  Ala  Tyr  Lys  Glu  Phe  Arg  Val  Val
      65                        70                       75

GAA  TTA  GAT  CCA  AGC  GCA  AAG  ATC  GAA  GTC  ACT  TAT  TAT  GAT  AAG  AAT     288
Glu  Leu  Asp  Pro  Ser  Ala  Lys  Ile  Glu  Val  Thr  Tyr  Tyr  Asp  Lys  Asn
 80                       85                       90                       95

AAG  AAA  AAA  GAA  GAA  ACG  AAG  TCT  TTC  CCT  ATA  ACA  GAA  AAA  GGT  TTT     336
Lys  Lys  Lys  Glu  Glu  Thr  Lys  Ser  Phe  Pro  Ile  Thr  Glu  Lys  Gly  Phe
                     100                      105                      110

GTT  GTC  CCA  GAT  TTA  TCA  GAG  CAT  ATT  AAA  AAC  CCT  GGA  TTC  AAC  TTA     384
Val  Val  Pro  Asp  Leu  Ser  Glu  His  Ile  Lys  Asn  Pro  Gly  Phe  Asn  Leu
                115                       120                      125

ATT  ACA  AAG  GTT  GTT  ATA  GAA  AAG  AAA  TAA                                    414
Ile  Thr  Lys  Val  Val  Ile  Glu  Lys  Lys   *
           130                       135
```

( 2 ) INFORMATION FOR SEQ ID NO: 6:

( i ) SEQUENCE CHARACTERISTICS:
        ( A ) LENGTH: 137 amino acids ( B ) TYPE: amino acid
( D ) TOPOLOGY: linear ( i i ) MOLECULE TYPE: protein ( x i ) SEQUENCE DESCRIPTION: SEQ ID NO: 6:

| Met | Ser | Ser | Ser | Phe | Asp | Lys | Gly | Lys | Tyr | Lys | Lys | Gly | Asp | Asp | Ala |
|-----|-----|-----|-----|-----|-----|-----|-----|-----|-----|-----|-----|-----|-----|-----|-----|
| -1  | 1   |     |     | 5   |     |     |     |     | 10  |     |     |     |     |     | 15  |

| Ser | Tyr | Phe | Glu | Pro | Thr | Gly | Pro | Tyr | Leu | Met | Val | Asn | Val | Thr | Gly |
|     |     |     |     | 20  |     |     |     |     | 25  |     |     |     |     | 30  |     |

| Val | Asp | Ser | Lys | Gly | Asn | Glu | Leu | Leu | Ser | Pro | His | Tyr | Val | Glu | Phe |
|     |     |     | 35  |     |     |     |     | 40  |     |     |     |     | 45  |     |     |

| Pro | Ile | Lys | Pro | Gly | Thr | Thr | Leu | Thr | Lys | Glu | Lys | Ile | Glu | Tyr | Tyr |
|     |     | 50  |     |     |     |     | 55  |     |     |     |     | 60  |     |     |     |

| Val | Glu | Trp | Ala | Leu | Asp | Ala | Thr | Ala | Tyr | Lys | Glu | Phe | Arg | Val | Val |
|     | 65  |     |     |     |     | 70  |     |     |     |     | 75  |     |     |     |     |

| Glu | Leu | Asp | Pro | Ser | Ala | Lys | Ile | Glu | Val | Thr | Tyr | Tyr | Asp | Lys | Asn |
| 80  |     |     |     |     | 85  |     |     |     |     | 90  |     |     |     |     | 95  |

| Lys | Lys | Lys | Glu | Glu | Thr | Lys | Ser | Phe | Pro | Ile | Thr | Glu | Lys | Gly | Phe |
|     |     |     |     | 100 |     |     |     |     | 105 |     |     |     |     | 110 |     |

| Val | Val | Pro | Asp | Leu | Ser | Glu | His | Ile | Lys | Asn | Pro | Gly | Phe | Asn | Leu |
|     |     |     | 115 |     |     |     |     | 120 |     |     |     |     | 125 |     |     |

| Ile | Thr | Lys | Val | Val | Ile | Glu | Lys | Lys |
|     |     | 130 |     |     |     |     | 135 |     |

( 2 ) INFORMATION FOR SEQ ID NO: 7:

( i ) SEQUENCE CHARACTERISTICS:
      ( A ) LENGTH: 384 base pairs
      ( B ) TYPE: nucleic acid
      ( C ) STRANDEDNESS: single
      ( D ) TOPOLOGY: linear ( i i ) MOLECULE TYPE: other nucleic acid
      ( A ) DESCRIPTION: /desc = "recombinant DNA"

( v i ) ORIGINAL SOURCE:
      ( A ) ORGANISM: Staphylococcus aureus
      ( B ) STRAIN: Phage 42D ( v i i i ) IMMEDIATE SOURCE:
      ( B ) CLONE: Plasmid pMET5

( i x ) FEATURE:
      ( A ) NAME/KEY: -
      ( B ) LOCATION: 1..3
      ( D ) OTHER INFORMATION:/note= "start codon"

( i x ) FEATURE:
      ( A ) NAME/KEY: CDS
      ( B ) LOCATION: 1..384

( i x ) FEATURE:
      ( A ) NAME/KEY: -
      ( B ) LOCATION: 382..384
      ( D ) OTHER INFORMATION:/note= "stop codon"

( i x ) FEATURE:
      ( A ) NAME/KEY: mat_peptide
      ( B ) LOCATION: 4..381
      ( D ) OTHER INFORMATION:/product="shortened mature
          protein"

( x i ) SEQUENCE DESCRIPTION: SEQ ID NO: 7:

```
ATG AAA GGC GAT GAC GCG AGT TAT TTT GAA CCA ACA GGC CCG TAT TTG     48
Met Lys Gly Asp Asp Ala Ser Tyr Phe Glu Pro Thr Gly Pro Tyr Leu
 -1   1           5                  10                  15

ATG GTA AAT GTG ACT GGA GTT GAT GGT AAA AGA AAT GAA TTG CTA TCC     96
```

|     |     |     |     |     |     |     |     |     |     |     |     |     |     |     |     |
|-----|-----|-----|-----|-----|-----|-----|-----|-----|-----|-----|-----|-----|-----|-----|-----|
| Met | Val | Asn | Val | Thr | Gly | Val | Asp | Gly | Lys | Arg | Asn | Glu | Leu | Leu | Ser |
|     |     |     | 20  |     |     |     |     |     | 25  |     |     |     |     | 30  |     |

| CCT | CGT | TAT | GTC | GAG | TTT | CCT | ATT | AAA | CCT | GGG | ACT | ACA | CTT | ACA | AAA | 144 |
|-----|-----|-----|-----|-----|-----|-----|-----|-----|-----|-----|-----|-----|-----|-----|-----|-----|
| Pro | Arg | Tyr | Val | Glu | Phe | Pro | Ile | Lys | Pro | Gly | Thr | Thr | Leu | Thr | Lys |     |
|     |     |     | 35  |     |     |     |     | 40  |     |     |     |     |     | 45  |     |     |

| GAA | AAA | ATT | GAA | TAC | TAT | GTC | GAA | TGG | GCA | TTA | GAT | GCG | ACA | GCA | TAT | 192 |
|-----|-----|-----|-----|-----|-----|-----|-----|-----|-----|-----|-----|-----|-----|-----|-----|-----|
| Glu | Lys | Ile | Glu | Tyr | Tyr | Val | Glu | Trp | Ala | Leu | Asp | Ala | Thr | Ala | Tyr |     |
|     |     | 50  |     |     |     |     | 55  |     |     |     |     | 60  |     |     |     |     |

| AAA | GAG | TTT | AGA | GTA | GTT | GAA | TTA | GAT | CCA | AGC | GCA | AAG | ATC | GAA | GTC | 240 |
|-----|-----|-----|-----|-----|-----|-----|-----|-----|-----|-----|-----|-----|-----|-----|-----|-----|
| Lys | Glu | Phe | Arg | Val | Val | Glu | Leu | Asp | Pro | Ser | Ala | Lys | Ile | Glu | Val |     |
|     | 65  |     |     |     |     | 70  |     |     |     |     | 75  |     |     |     |     |     |

| ACT | TAT | TAT | GAT | AAG | AAT | AAG | AAA | AAA | GAA | GAA | ACG | AAG | TCT | TTC | CCT | 288 |
|-----|-----|-----|-----|-----|-----|-----|-----|-----|-----|-----|-----|-----|-----|-----|-----|-----|
| Thr | Tyr | Tyr | Asp | Lys | Asn | Lys | Lys | Lys | Glu | Glu | Thr | Lys | Ser | Phe | Pro |     |
| 80  |     |     |     |     | 85  |     |     |     |     | 90  |     |     |     |     | 95  |     |

| ATA | ACA | GAA | AAA | GGT | TTT | GTT | GTC | CCA | GAT | TTA | TCA | GAG | CAT | ATT | AAA | 336 |
|-----|-----|-----|-----|-----|-----|-----|-----|-----|-----|-----|-----|-----|-----|-----|-----|-----|
| Ile | Thr | Glu | Lys | Gly | Phe | Val | Val | Pro | Asp | Leu | Ser | Glu | His | Ile | Lys |     |
|     |     |     |     | 100 |     |     |     |     | 105 |     |     |     |     | 110 |     |     |

| AAC | CCT | GGA | TTC | AAC | TTA | ATT | ACM | AAG | GTT | GTT | ATA | GAA | AAG | AAA | TAA | 384 |
|-----|-----|-----|-----|-----|-----|-----|-----|-----|-----|-----|-----|-----|-----|-----|-----|-----|
| Asn | Pro | Gly | Phe | Asn | Leu | Ile | Thr | Lys | Val | Val | Ile | Glu | Lys | Lys | *   |     |
|     |     |     | 115 |     |     |     |     | 120 |     |     |     |     |     | 125 |     |     |

( 2 ) INFORMATION FOR SEQ ID NO: 8:

( i ) SEQUENCE CHARACTERISTICS:
        ( A ) LENGTH: 127 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 8:

|     |     |     |     |     |     |     |     |     |     |     |     |     |     |     |
|-----|-----|-----|-----|-----|-----|-----|-----|-----|-----|-----|-----|-----|-----|-----|
| Met | Lys | Gly | Asp | Asp | Ala | Ser | Tyr | Phe | Glu | Pro | Thr | Gly | Pro | Tyr | Leu |
| - 1 | 1   |     |     |     | 5   |     |     |     |     | 10  |     |     |     |     | 15  |

|     |     |     |     |     |     |     |     |     |     |     |     |     |     |     |     |
|-----|-----|-----|-----|-----|-----|-----|-----|-----|-----|-----|-----|-----|-----|-----|-----|
| Met | Val | Asn | Val | Thr | Gly | Val | Asp | Gly | Lys | Arg | Asn | Glu | Leu | Leu | Ser |
|     |     |     | 20  |     |     |     |     |     | 25  |     |     |     |     | 30  |     |

|     |     |     |     |     |     |     |     |     |     |     |     |     |     |     |
|-----|-----|-----|-----|-----|-----|-----|-----|-----|-----|-----|-----|-----|-----|-----|
| Pro | Arg | Tyr | Val | Glu | Phe | Pro | Ile | Lys | Pro | Gly | Thr | Thr | Leu | Thr | Lys |
|     |     |     | 35  |     |     |     |     | 40  |     |     |     |     |     | 45  |     |

|     |     |     |     |     |     |     |     |     |     |     |     |     |     |     |
|-----|-----|-----|-----|-----|-----|-----|-----|-----|-----|-----|-----|-----|-----|-----|
| Glu | Lys | Ile | Glu | Tyr | Tyr | Val | Glu | Trp | Ala | Leu | Asp | Ala | Thr | Ala | Tyr |
|     |     | 50  |     |     |     |     | 55  |     |     |     |     | 60  |     |     |     |

|     |     |     |     |     |     |     |     |     |     |     |     |     |     |     |
|-----|-----|-----|-----|-----|-----|-----|-----|-----|-----|-----|-----|-----|-----|-----|
| Lys | Glu | Phe | Arg | Val | Val | Glu | Leu | Asp | Pro | Ser | Ala | Lys | Ile | Glu | Val |
|     | 65  |     |     |     |     | 70  |     |     |     |     | 75  |     |     |     |     |

|     |     |     |     |     |     |     |     |     |     |     |     |     |     |     |
|-----|-----|-----|-----|-----|-----|-----|-----|-----|-----|-----|-----|-----|-----|-----|
| Thr | Tyr | Tyr | Asp | Lys | Asn | Lys | Lys | Lys | Glu | Glu | Thr | Lys | Ser | Phe | Pro |
| 80  |     |     |     |     | 85  |     |     |     |     | 90  |     |     |     |     | 95  |

|     |     |     |     |     |     |     |     |     |     |     |     |     |     |     |
|-----|-----|-----|-----|-----|-----|-----|-----|-----|-----|-----|-----|-----|-----|-----|
| Ile | Thr | Glu | Lys | Gly | Phe | Val | Val | Pro | Asp | Leu | Ser | Glu | His | Ile | Lys |
|     |     |     |     | 100 |     |     |     |     | 105 |     |     |     |     | 110 |     |

|     |     |     |     |     |     |     |     |     |     |     |     |     |     |
|-----|-----|-----|-----|-----|-----|-----|-----|-----|-----|-----|-----|-----|-----|
| Asn | Pro | Gly | Phe | Asn | Leu | Ile | Thr | Lys | Val | Val | Ile | Glu | Lys | Lys |
|     |     |     | 115 |     |     |     |     | 120 |     |     |     |     |     | 125 |

( 2 ) INFORMATION FOR SEQ ID NO: 9:

( i ) SEQUENCE CHARACTERISTICS:
        ( A ) LENGTH: 372 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "recombinant DNA"

( v i ) ORIGINAL SOURCE:
        ( A ) ORGANISM: Staphylococcus aureus
        ( B ) STRAIN: Phage 42D ( v i i ) IMMEDIATE SOURCE:

( B ) CLONE: Plasmid pMET5

( i x ) FEATURE:
    ( A ) NAME/KEY: -
    ( B ) LOCATION: 1..3
    ( D ) OTHER INFORMATION:/note= "start codon"

( i x ) FEATURE:
    ( A ) NAME/KEY: CDS
    ( B ) LOCATION: 1..372

( i x ) FEATURE:
    ( A ) NAME/KEY: -
    ( B ) LOCATION: 370..372
    ( D ) OTHER INFORMATION:/note= "stop codon"

( i x ) FEATURE:
    ( A ) NAME/KEY: mat_peptide
    ( B ) LOCATION: 4..369
    ( D ) OTHER INFORMATION:/product="shortened mature protein"

( x i ) SEQUENCE DESCRIPTION: SEQ ID NO: 9:

| | | | | | | | | | | | | | | | | |
|---|---|---|---|---|---|---|---|---|---|---|---|---|---|---|---|---|
| ATG | GCG | AGT | TAT | TTT | GAA | CCA | ACA | GGC | CCG | TAT | TTG | ATG | GTA | AAT | GTG | 48 |
| Met | Ala | Ser | Tyr | Phe | Glu | Pro | Thr | Gly | Pro | Tyr | Leu | Met | Val | Asn | Val | |
| -1 | 1 | | | 5 | | | | | | 10 | | | | | 15 | |
| ACT | GGA | GTT | GAT | GGT | AAA | AGA | AAT | GAA | TTG | CTA | TCC | CCT | CGT | TAT | GTC | 96 |
| Thr | Gly | Val | Asp | Gly | Lys | Arg | Asn | Glu | Leu | Leu | Ser | Pro | Arg | Tyr | Val | |
| | | | | 20 | | | | | 25 | | | | | 30 | | |
| GAG | TTT | CCT | ATT | AAA | CCT | GGG | ACT | ACA | CTT | ACA | AAA | GAA | AAA | ATT | GAA | 144 |
| Glu | Phe | Pro | Ile | Lys | Pro | Gly | Thr | Thr | Leu | Thr | Lys | Glu | Lys | Ile | Glu | |
| | | | 35 | | | | | 40 | | | | | 45 | | | |
| TAC | TAT | GTC | GAA | TGG | GCA | TTA | GAT | GCG | ACA | GCA | TAT | AAA | GAG | TTT | AGA | 192 |
| Tyr | Tyr | Val | Glu | Trp | Ala | Leu | Asp | Ala | Thr | Ala | Tyr | Lys | Glu | Phe | Arg | |
| | | 50 | | | | | 55 | | | | | 60 | | | | |
| GTA | GTT | GAA | TTA | GAT | CCA | AGC | GCA | AAG | ATC | GAA | GTC | ACT | TAT | TAT | GAT | 240 |
| Val | Val | Glu | Leu | Asp | Pro | Ser | Ala | Lys | Ile | Glu | Val | Thr | Tyr | Tyr | Asp | |
| | 65 | | | | | 70 | | | | | 75 | | | | | |
| AAG | AAT | AAG | AAA | AAA | GAA | GAA | ACG | AAG | TCT | TTC | CCT | ATA | ACA | GAA | AAA | 288 |
| Lys | Asn | Lys | Lys | Lys | Glu | Glu | Thr | Lys | Ser | Phe | Pro | Ile | Thr | Glu | Lys | |
| 80 | | | | | 85 | | | | | 90 | | | | | 95 | |
| GGT | TTT | GTT | GTC | CCA | GAT | TTA | TCA | GAG | CAT | ATT | AAA | AAC | CCT | GGA | TTC | 336 |
| Gly | Phe | Val | Val | Pro | Asp | Leu | Ser | Glu | His | Ile | Lys | Asn | Pro | Gly | Phe | |
| | | | | 100 | | | | | 105 | | | | | 110 | | |
| AAC | TTA | ATT | ACM | AAG | GTT | GTT | ATA | GAA | AAG | AAA | TAA | | | | | 372 |
| Asn | Leu | Ile | Thr | Lys | Val | Val | Ile | Glu | Lys | Lys | * | | | | | |
| | | | 115 | | | | | 120 | | | | | | | | |

( 2 ) INFORMATION FOR SEQ ID NO: 10:

( i ) SEQUENCE CHARACTERISTICS:
        ( A ) LENGTH: 123 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 10:

| | | | | | | | | | | | | | | |
|---|---|---|---|---|---|---|---|---|---|---|---|---|---|---|
| Met | Ala | Ser | Tyr | Phe | Glu | Pro | Thr | Gly | Pro | Tyr | Leu | Met | Val | Asn | Val |
| -1 | 1 | | | 5 | | | | | | 10 | | | | | 15 |
| Thr | Gly | Val | Asp | Gly | Lys | Arg | Asn | Glu | Leu | Leu | Ser | Pro | Arg | Tyr | Val |
| | | | | 20 | | | | | 25 | | | | | 30 | |
| Glu | Phe | Pro | Ile | Lys | Pro | Gly | Thr | Thr | Leu | Thr | Lys | Glu | Lys | Ile | Glu |
| | | | 35 | | | | | 40 | | | | | 45 | | |
| Tyr | Tyr | Val | Glu | Trp | Ala | Leu | Asp | Ala | Thr | Ala | Tyr | Lys | Glu | Phe | Arg |
| | | 50 | | | | | 55 | | | | | 60 | | | |

```
         Val  Val  Glu  Leu  Asp  Pro  Ser  Ala  Lys  Ile  Glu  Val  Thr  Tyr  Tyr  Asp
              65                  70                       75

Lys  Asn  Lys  Lys  Lys  Glu  Glu  Thr  Lys  Ser  Phe  Pro  Ile  Thr  Glu  Lys
              80                  85                       90                         95

Gly  Phe  Val  Val  Pro  Asp  Leu  Ser  Glu  His  Ile  Lys  Asn  Pro  Gly  Phe
                             100                      105                      110

Asn  Leu  Ile  Thr  Lys  Val  Val  Ile  Glu  Lys  Lys
                        115                  120
```

( 2 ) INFORMATION FOR SEQ ID NO: 11:

( i ) SEQUENCE CHARACTERISTICS:
        ( A ) LENGTH: 414 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "recombinant DNA"

( v i ) ORIGINAL SOURCE:
        ( A ) ORGANISM: Staphylococcus aureus
        ( B ) STRAIN: Phage 42D ( v i i ) IMMEDIATE SOURCE:
        ( B ) CLONE: Plasmid pMET5

( i x ) FEATURE:
        ( A ) NAME/KEY: CDS
        ( B ) LOCATION:1..414

( i x ) FEATURE:
        ( A ) NAME/KEY: -
        ( B ) LOCATION:1..3
        ( D ) OTHER INFORMATION:/note= "start codon"

( i x ) FEATURE:
        ( A ) NAME/KEY: -
        ( B ) LOCATION:412..414
        ( D ) OTHER INFORMATION:/note= "stop codon"

( i x ) FEATURE:
        ( A ) NAME/KEY: mat_peptide
        ( B ) LOCATION:4..411
        ( D ) OTHER INFORMATION:/product="mature protein"

( x i ) SEQUENCE DESCRIPTION: SEQ ID NO: 11:

```
ATG  TCA  AGT  TCA  TTC  GAC  AAA  GGA  AAA  TAT  AAA  AAA  GGC  GAT  GAC  GCG          48
Met  Ser  Ser  Ser  Phe  Asp  Lys  Gly  Lys  Tyr  Lys  Lys  Gly  Asp  Asp  Ala
- 1    1              5                       10                        15

AGT  TAT  TTT  GAA  CCA  ACA  GGC  CCG  TAT  TTG  TGY  GTA  AAT  GTG  ACT  GGA          96
Ser  Tyr  Phe  Glu  Pro  Thr  Gly  Pro  Tyr  Leu  Cys  Val  Asn  Val  Thr  Gly
                        20                       25                        30

GTY  GAY  GGT  AAA  AGA  AAT  GAR  CTS  YTR  TCC  CCK  CGK  TAT  GTC  GAG  TTT         144
Val  Asp  Gly  Lys  Arg  Asn  Glu  Leu  Leu  Ser  Pro  Arg  Tyr  Val  Glu  Phe
                    35                       40                        45

CCT  ATT  AAA  CCT  GGG  ACT  ACA  CTT  ACA  AAA  GAA  AAA  ATT  GAA  TAC  TAT         192
Pro  Ile  Lys  Pro  Gly  Thr  Thr  Leu  Thr  Lys  Glu  Lys  Ile  Glu  Tyr  Tyr
               50                       55                        60

GTC  GAA  TGG  GCA  TTA  GAT  GCG  ACA  GCA  TAT  AAA  GAG  TTT  AGA  GTA  GTT         240
Val  Glu  Trp  Ala  Leu  Asp  Ala  Thr  Ala  Tyr  Lys  Glu  Phe  Arg  Val  Val
          65                       70                        75

GAA  TTA  GAT  CCA  AGC  GCA  AAG  ATC  GAA  GTC  ACT  TAT  TAT  GAT  AAG  AAT         288
Glu  Leu  Asp  Pro  Ser  Ala  Lys  Ile  Glu  Val  Thr  Tyr  Tyr  Asp  Lys  Asn
     80                       85                        90                         95

AAG  AAA  AAA  GAA  GAA  ACG  AAG  TCT  TTC  CCT  ATA  ACA  GAA  AAA  GGT  TTT         336
Lys  Lys  Lys  Glu  Glu  Thr  Lys  Ser  Phe  Pro  Ile  Thr  Glu  Lys  Gly  Phe
                    100                      105                       110
```

| GTT | GTC | CCA | GAT | TTA | TCA | GAG | CAT | ATT | AAA | AAC | CCT | GGA | TTC | AAC | TTA | 384 |
| Val | Val | Pro | Asp | Leu | Ser | Glu | His | Ile | Lys | Asn | Pro | Gly | Phe | Asn | Leu | |
| | | | 115 | | | | 120 | | | | | 125 | | | | |

| ATT | ACC | AAG | GTT | GTT | ATA | GAA | AAG | AAA | TAA | 414 |
| Ile | Thr | Lys | Val | Val | Ile | Glu | Lys | Lys | * | |
| | | 130 | | | | 135 | | | | |

( 2 ) INFORMATION FOR SEQ ID NO: 12:

( i ) SEQUENCE CHARACTERISTICS:
        ( A ) LENGTH: 137 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 12:

| Met | Ser | Ser | Ser | Phe | Asp | Lys | Gly | Lys | Tyr | Lys | Lys | Gly | Asp | Asp | Ala |
| -1 | 1 | | | | 5 | | | | 10 | | | | | | 15 |

| Ser | Tyr | Phe | Glu | Pro | Thr | Gly | Pro | Tyr | Leu | Cys | Val | Asn | Val | Thr | Gly |
| | | | | 20 | | | | | 25 | | | | | 30 | |

| Val | Asp | Gly | Lys | Arg | Asn | Glu | Leu | Leu | Ser | Pro | Arg | Tyr | Val | Glu | Phe |
| | | | 35 | | | | | 40 | | | | | 45 | | |

| Pro | Ile | Lys | Pro | Gly | Thr | Thr | Leu | Thr | Lys | Glu | Lys | Ile | Glu | Tyr | Tyr |
| | | 50 | | | | | 55 | | | | | 60 | | | |

| Val | Glu | Trp | Ala | Leu | Asp | Ala | Thr | Ala | Tyr | Lys | Glu | Phe | Arg | Val | Val |
| | 65 | | | | | 70 | | | | | 75 | | | | |

| Glu | Leu | Asp | Pro | Ser | Ala | Lys | Ile | Glu | Val | Thr | Tyr | Tyr | Asp | Lys | Asn |
| 80 | | | | | 85 | | | | | 90 | | | | | 95 |

| Lys | Lys | Lys | Glu | Glu | Thr | Lys | Ser | Phe | Pro | Ile | Thr | Glu | Lys | Gly | Phe |
| | | | | 100 | | | | | 105 | | | | | 110 | |

| Val | Val | Pro | Asp | Leu | Ser | Glu | His | Ile | Lys | Asn | Pro | Gly | Phe | Asn | Leu |
| | | | 115 | | | | 120 | | | | | 125 | | | |

| Ile | Thr | Lys | Val | Val | Ile | Glu | Lys | Lys |
| | | 130 | | | | 135 | | |

( 2 ) INFORMATION FOR SEQ ID NO: 13:

( i ) SEQUENCE CHARACTERISTICS:
        ( A ) LENGTH: 414 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "recombinant DNA"

( v i ) ORIGINAL SOURCE:
        ( A ) ORGANISM: Staphylococcus aureus
        ( B ) STRAIN: Phage 42D ( v i i i ) IMMEDIATE SOURCE:
        ( B ) CLONE: Plasmid pMET5

( i x ) FEATURE:
        ( A ) NAME/KEY: mat_peptide
        ( B ) LOCATION: 4..411
        ( D ) OTHER INFORMATION: /product="mature protein"

( i x ) FEATURE:
        ( A ) NAME/KEY: -
        ( B ) LOCATION: 1..3
        ( D ) OTHER INFORMATION: /note= "start codon"

( i x ) FEATURE:
        ( A ) NAME/KEY: -
        ( B ) LOCATION: 412..414
        ( D ) OTHER INFORMATION: /note= "stop codon"

( i x ) FEATURE:
  ( A ) NAME/KEY: CDS
  ( B ) LOCATION: 1..414

( x i ) SEQUENCE DESCRIPTION: SEQ ID NO: 13:

```
ATG TCA AGT TCA TTC GAC AAA GGA AAA TAT AAA AAA GGC GAT GAC GCG      48
Met Ser Ser Ser Phe Asp Lys Gly Lys Tyr Lys Lys Gly Asp Asp Ala
 -1   1               5                  10                  15

AGT TAT TTT GAA CCA ACA GGC CCG TAT TTG CTA GTA AAT GTG ACT GGA      96
Ser Tyr Phe Glu Pro Thr Gly Pro Tyr Leu Leu Val Asn Val Thr Gly
                 20                  25                  30

GYT GAY GGT AAA AGA AAT GAR CTS YTR TCC CCK CGK TAT GTC GAG TTT     144
Val Asp Gly Lys Arg Asn Glu Leu Leu Ser Pro Arg Tyr Val Glu Phe
             35                  40                  45

CCT ATT AAA CCT GGG ACT ACA CTT ACA AAA GAA AAA ATT GAA TAC TAT     192
Pro Ile Lys Pro Gly Thr Thr Leu Thr Lys Glu Lys Ile Glu Tyr Tyr
         50                  55                  60

GTC GAA TGG GCA TTA GAT GCG ACA GCA TAT AAA GAG TTT AGA GTA GTT     240
Val Glu Trp Ala Leu Asp Ala Thr Ala Tyr Lys Glu Phe Arg Val Val
     65                  70                  75

GAA TTA GAT CCA AGC GCA AAG ATC GAA GTC ACT TAT TAT GAT AAG AAT     288
Glu Leu Asp Pro Ser Ala Lys Ile Glu Val Thr Tyr Tyr Asp Lys Asn
 80                  85                  90                  95

AAG AAA AAA GAA GAA ACG AAG TCT TTC CCT ATA ACA GAA AAA GGT TTT     336
Lys Lys Lys Glu Glu Thr Lys Ser Phe Pro Ile Thr Glu Lys Gly Phe
                    100                 105                 110

GTT GTC CCA GAT TTA TCA GAG CAT ATT AAA AAC CCT GGA TTC AAC TTA     384
Val Val Pro Asp Leu Ser Glu His Ile Lys Asn Pro Gly Phe Asn Leu
                115                 120                 125

ATT ACM AAG GTT GTT ATA GAA AAG AAA TAA                             414
Ile Thr Lys Val Val Ile Glu Lys Lys *
            130                 135
```

( 2 ) INFORMATION FOR SEQ ID NO: 14:

( i ) SEQUENCE CHARACTERISTICS:
    ( A ) LENGTH: 137 amino acids
    ( B ) TYPE: amino acid
    ( D ) TOPOLOGY: linear ( i i ) MOLECULE TYPE: protein ( x i ) SEQUENCE DESCRIPTION: SEQ ID NO: 14:

```
Met Ser Ser Ser Phe Asp Lys Gly Lys Tyr Lys Lys Gly Asp Asp Ala
 -1   1               5                  10                  15

Ser Tyr Phe Glu Pro Thr Gly Pro Tyr Leu Leu Val Asn Val Thr Gly
                 20                  25                  30

Val Asp Gly Lys Arg Asn Glu Leu Leu Ser Pro Arg Tyr Val Glu Phe
             35                  40                  45

Pro Ile Lys Pro Gly Thr Thr Leu Thr Lys Glu Lys Ile Glu Tyr Tyr
         50                  55                  60

Val Glu Trp Ala Leu Asp Ala Thr Ala Tyr Lys Glu Phe Arg Val Val
     65                  70                  75

Glu Leu Asp Pro Ser Ala Lys Ile Glu Val Thr Tyr Tyr Asp Lys Asn
 80                  85                  90                  95

Lys Lys Lys Glu Glu Thr Lys Ser Phe Pro Ile Thr Glu Lys Gly Phe
                    100                 105                 110

Val Val Pro Asp Leu Ser Glu His Ile Lys Asn Pro Gly Phe Asn Leu
                115                 120                 125

Ile Thr Lys Val Val Ile Glu Lys Lys
```

( 2 ) INFORMATION FOR SEQ ID NO: 15:

( i ) SEQUENCE CHARACTERISTICS:
  ( A ) LENGTH: 29 base pairs
  ( B ) TYPE: nucleic acid
  ( C ) STRANDEDNESS: single
  ( D ) TOPOLOGY: linear ( i i ) MOLECULE TYPE: other nucleic acid
  ( A ) DESCRIPTION: /desc = "synthetic DNA (from oligonucleotide synthesis)"

( i x ) FEATURE:
  ( A ) NAME/KEY: RBS
  ( B ) LOCATION:1..4
  ( D ) OTHER INFORMATION:/note= "ribosome binding site 1"

( i x ) FEATURE:
  ( A ) NAME/KEY: RBS
  ( B ) LOCATION:15..20
  ( D ) OTHER INFORMATION:/note= "ribosome binding site 2"

( i x ) FEATURE:
  ( A ) NAME/KEY: -
  ( B ) LOCATION:27..29
  ( D ) OTHER INFORMATION:/note= "translation start codon"

( x i ) SEQUENCE DESCRIPTION: SEQ ID NO: 15:

AGGAAACAGA ATTCAGGAGG CCTCATATG   29

( 2 ) INFORMATION FOR SEQ ID NO: 16:

( i ) SEQUENCE CHARACTERISTICS:
  ( A ) LENGTH: 1023 base pairs
  ( B ) TYPE: nucleic acid
  ( C ) STRANDEDNESS: single
  ( D ) TOPOLOGY: linear ( i i ) MOLECULE TYPE: DNA (genomic)

( v i ) ORIGINAL SOURCE:
  ( A ) ORGANISM: Staphylococcus aureus
  ( B ) STRAIN: Phage 42D ( v i i ) IMMEDIATE SOURCE:
  ( B ) CLONE: Plasmid DB17

( i x ) FEATURE:
  ( A ) NAME/KEY: -35_signal
  ( B ) LOCATION:224..229

( i x ) FEATURE:
  ( A ) NAME/KEY: -10_signal
  ( B ) LOCATION:248..253

( i x ) FEATURE:
  ( A ) NAME/KEY: -
  ( B ) LOCATION:332..336
  ( D ) OTHER INFORMATION:/note= "Shine-Dalgarno sequence"

( i x ) FEATURE:
  ( A ) NAME/KEY: sig_peptide
  ( B ) LOCATION:344..415

( i x ) FEATURE:
  ( A ) NAME/KEY: mat_peptide
  ( B ) LOCATION:416..832
  ( D ) OTHER INFORMATION:/product="mature protein SAK42D"

( i x ) FEATURE:
  ( A ) NAME/KEY: CDS
  ( B ) LOCATION:344..835

( x i ) SEQUENCE DESCRIPTION: SEQ ID NO: 16:

```
ACTAACTATA GATTCGATGT TGGACAGGCT GTATACGCGC CTGGAACATT AATATATGTG    60

TTTGAAATTA TAGATGGTTG TTGTCGCATT TATTGGAACA ATCATAATGA GTGGATATGG   120

CATGAGAGAT TGATTGTGAA AGAAGTGTTT TAATTCTAAG GTTAAAATGT TAAATATTTG   180

TTAATTATTT TTTAATGTAA GTTTAGTTTC TTTTAATATT TTATTGATTT TAATATTTT    240

CTCAATATAA AATGAAGTTG TTGATATTTA TCATCTTAAA TAAGGGTGTT AGCTATAAAA   300

AGAGATAAAT AAAAACAAAT ATATTATATT TGGAGGAAGC GCC ATG CTC AAA AGA    355
                                              Met Leu Lys Arg
                                              -24
```

| | | | | | | | | | | | | | | | | |
|---|---|---|---|---|---|---|---|---|---|---|---|---|---|---|---|---|
| AGT | TTA | TTA | TTT | TTA | ACT | GTT | TTA | TTG | TTA | TTA | TTC | TCA | TTT | TCT | TCA | 403 |
| Ser | Leu | Leu | Phe | Leu | Thr | Val | Leu | Leu | Leu | Leu | Phe | Ser | Phe | Ser | Ser | |
| -20 | | | | -15 | | | | | -10 | | | | | -5 | | |
| ATT | ACT | AAT | GAG | GTA | AGT | GCA | TCA | AGT | TCA | TTC | GAC | AAA | GGA | AAA | TAT | 451 |
| Ile | Thr | Asn | Glu | Val | Ser | Ala | Ser | Ser | Ser | Phe | Asp | Lys | Gly | Lys | Tyr | |
| | | | | 1 | | | | 5 | | | | | | 10 | | |
| AAA | AAA | GGC | GAT | GAC | GCG | AGT | TAT | TTT | GAA | CCA | ACA | GGC | CCG | TAT | TTG | 499 |
| Lys | Lys | Gly | Asp | Asp | Ala | Ser | Tyr | Phe | Glu | Pro | Thr | Gly | Pro | Tyr | Leu | |
| | | 15 | | | | | 20 | | | | | 25 | | | | |
| ATG | GTA | AAT | GTG | ACT | GGA | GTT | GAT | GGT | AAA | AGA | AAT | GAA | TTG | CTA | TCC | 547 |
| Met | Val | Asn | Val | Thr | Gly | Val | Asp | Gly | Lys | Arg | Asn | Glu | Leu | Leu | Ser | |
| | 30 | | | | | 35 | | | | | 40 | | | | | |
| CCT | CGT | TAT | GTC | GAG | TTT | CCT | ATT | AAA | CCT | GGG | ACT | ACA | CTT | ACA | AAA | 595 |
| Pro | Arg | Tyr | Val | Glu | Phe | Pro | Ile | Lys | Pro | Gly | Thr | Thr | Leu | Thr | Lys | |
| 45 | | | | 50 | | | | | 55 | | | | | 60 | | |
| GAA | AAA | ATT | GAA | TAC | TAT | GTC | GAA | TGG | GCA | TTA | GAT | GCG | ACA | GCA | TAT | 643 |
| Glu | Lys | Ile | Glu | Tyr | Tyr | Val | Glu | Trp | Ala | Leu | Asp | Ala | Thr | Ala | Tyr | |
| | | | 65 | | | | | 70 | | | | | 75 | | | |
| AAA | GAG | TTT | AGA | GTA | GTT | GAA | TTA | GAT | CCA | AGC | GCA | AAG | ATC | GAA | GTC | 691 |
| Lys | Glu | Phe | Arg | Val | Val | Glu | Leu | Asp | Pro | Ser | Ala | Lys | Ile | Glu | Val | |
| | | | 80 | | | | | 85 | | | | | 90 | | | |
| ACT | TAT | TAT | GAT | AAG | AAT | AAG | AAA | AAA | GAA | GAA | ACG | AAG | TCT | TTC | CCT | 739 |
| Thr | Tyr | Tyr | Asp | Lys | Asn | Lys | Lys | Lys | Glu | Glu | Thr | Lys | Ser | Phe | Pro | |
| | | 95 | | | | | 100 | | | | | 105 | | | | |
| ATA | ACA | GAA | AAA | GGT | TTT | GTT | GTC | CCA | GAT | TTA | TCA | GAG | CAT | ATT | AAA | 787 |
| Ile | Thr | Glu | Lys | Gly | Phe | Val | Val | Pro | Asp | Leu | Ser | Glu | His | Ile | Lys | |
| | 110 | | | | | 115 | | | | | 120 | | | | | |
| AAC | CCT | GGA | TTC | AAC | TTA | ATT | ACA | AAG | GTT | GTT | ATA | GAA | AAG | AAA | TAA | 835 |
| Asn | Pro | Gly | Phe | Asn | Leu | Ile | Thr | Lys | Val | Val | Ile | Glu | Lys | Lys | * | |
| 125 | | | | 130 | | | | | 135 | | | | | 140 | | |

```
AACAAAATAG TTGTTTATTA TAGAAAGCAA TGTCTTGCTT GAATATGTGT AGTGAAAA     895

ATCTTTCATC AAATTCTCAT TCATGCACGA ATGGCTCTTC CCCACCTAAT CAGATATT     955

GTGACTTATG GGGAGAAATC AGTTAGGATA AAAAGTGGAT AATCCTTTTT TTAGGCA     1015

TCCAGGCA                                                            1023
```

(2) INFORMATION FOR SEQ ID NO: 17:

(i) SEQUENCE CHARACTERISTICS:
        (A) LENGTH: 163 amino acids
        (B) TYPE: amino acid
        (D) TOPOLOGY: linear (ii) MOLECULE TYPE: protein (xi) SEQUENCE DESCRIPTION: SEQ ID NO: 17:

```
Met Leu Lys Arg Ser Leu Leu Phe Leu Thr Val Leu Leu Leu Leu Phe
-24             -20                 -15                 -10

Ser Phe Ser Ser Ile Thr Asn Glu Val Ser Ala Ser Ser Ser Phe Asp
        -5              1                   5
```

|   |   |   |   |   |   |   |   |   |   |   |   |   |   |
|---|---|---|---|---|---|---|---|---|---|---|---|---|---|
| Lys | Gly | Lys | Tyr | Lys | Lys | Gly | Asp | Asp | Ala | Ser | Tyr | Phe | Glu | Pro | Thr |
|  | 10 |  |  |  | 15 |  |  |  |  | 20 |  |  |  |
| Gly | Pro | Tyr | Leu | Met | Val | Asn | Val | Thr | Gly | Val | Asp | Gly | Lys | Arg | Asn |
| 25 |  |  |  | 30 |  |  |  |  | 35 |  |  |  |  | 40 |
| Glu | Leu | Leu | Ser | Pro | Arg | Tyr | Val | Glu | Phe | Pro | Ile | Lys | Pro | Gly | Thr |
|  |  |  |  | 45 |  |  |  |  | 50 |  |  |  |  | 55 |
| Thr | Leu | Thr | Lys | Glu | Lys | Ile | Glu | Tyr | Tyr | Val | Glu | Trp | Ala | Leu | Asp |
|  |  |  | 60 |  |  |  |  | 65 |  |  |  |  | 70 |
| Ala | Thr | Ala | Tyr | Lys | Glu | Phe | Arg | Val | Val | Glu | Leu | Asp | Pro | Ser | Ala |
|  |  | 75 |  |  |  |  | 80 |  |  |  |  | 85 |
| Lys | Ile | Glu | Val | Thr | Tyr | Tyr | Asp | Lys | Asn | Lys | Lys | Glu | Glu | Thr |
|  | 90 |  |  |  |  | 95 |  |  |  | 100 |
| Lys | Ser | Phe | Pro | Ile | Thr | Glu | Lys | Gly | Phe | Val | Val | Pro | Asp | Leu | Ser |
| 105 |  |  |  |  | 110 |  |  |  |  | 115 |  |  |  |  | 120 |
| Glu | His | Ile | Lys | Asn | Pro | Gly | Phe | Asn | Leu | Ile | Thr | Lys | Val | Val | Ile |
|  |  |  |  | 125 |  |  |  |  | 130 |  |  |  |  | 135 |
| Glu | Lys | Lys |

(2) INFORMATION FOR SEQ ID NO: 18:

(i) SEQUENCE CHARACTERISTICS:
(A) LENGTH: 36 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic DNA from oligonucleotide synthesis"

(xi) SEQUENCE DESCRIPTION: SEQ ID NO: 18:

AGCTTGAATT CAGGAGGCCT CATATGTCAA GTTCAT            36

(2) INFORMATION FOR SEQ ID NO: 19:

(i) SEQUENCE CHARACTERISTICS:
(A) LENGTH: 36 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic DNA from oligonucleotide synthesis"

(xi) SEQUENCE DESCRIPTION: SEQ ID NO: 19:

TCGAATGAAC TTGACATATG AGGCCTCCTG AATTCA            36

(2) INFORMATION FOR SEQ ID NO: 20:

(i) SEQUENCE CHARACTERISTICS:
(A) LENGTH: 45 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic DNA from oligonucleotide synthesis"

(xi) SEQUENCE DESCRIPTION: SEQ ID NO: 20:

ATTCAACTTA ATTACAAAGG TTGTTATAGA AAAGAAATAA CTGCA            45

(2) INFORMATION FOR SEQ ID NO: 21:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "synthetic DNA from oligonucleotide synthesis"

( x i ) SEQUENCE DESCRIPTION: SEQ ID NO: 21:

GTTATTTCTT TTCTATAACA ACCTTTGTAA TTAAGTTG        38

( 2 ) INFORMATION FOR SEQ ID NO: 22:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "synthetic DNA from oligonucleotide synthesis"

( x i ) SEQUENCE DESCRIPTION: SEQ ID NO: 22:

CCTCATATGA AAGGCGATGA CG        22

( 2 ) INFORMATION FOR SEQ ID NO: 23:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "synthetic DNA from oligonucleotide synthesis"

( x i ) SEQUENCE DESCRIPTION: SEQ ID NO: 23:

CGTCATCGCC TTTCATATGA GG        22

( 2 ) INFORMATION FOR SEQ ID NO: 24:

( i ) SEQUENCE CHARACTERISTICS:
    ( A ) LENGTH: 31 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "synthetic DNA from oligonucleotide synthesis"

( x i ) SEQUENCE DESCRIPTION: SEQ ID NO: 24:

CCTCATATGG CGAGTTATTT TGAACCACAG G        31

( 2 ) INFORMATION FOR SEQ ID NO: 25:

( i ) SEQUENCE CHARACTERISTICS:
    ( A ) LENGTH: 31 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "synthetic DNA from oligonucleotide synthesis"

( x i ) SEQUENCE DESCRIPTION: SEQ ID NO: 25:

```
CCTGTGGTTC AAAATAACTC GCCATATGAG G                                        31
```

( 2 ) INFORMATION FOR SEQ ID NO: 26:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "synthetic DNA from
             oligonucleotide synthesis"

( x i ) SEQUENCE DESCRIPTION: SEQ ID NO: 26:

```
AATTCAGGAG GCCTCATATG TCAAGTTCAT TCGAAG                                   36
```

( 2 ) INFORMATION FOR SEQ ID NO: 27:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "synthetic DNA from
             oligonucleotide synthesis"

( x i ) SEQUENCE DESCRIPTION: SEQ ID NO: 27:

```
GATCCTTCGA ATGAACTTGA CATATGAGGC CTCCTG                                   36
```

( 2 ) INFORMATION FOR SEQ ID NO: 28:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "synthetic DNA from
             oligonucleotide synthesis"

( x i ) SEQUENCE DESCRIPTION: SEQ ID NO: 28:

```
CGACAAAGGA AAATTTAAAA AAGGCGAT                                            28
```

( 2 ) INFORMATION FOR SEQ ID NO: 29:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "synthetic DNA from
             oligonucleotide synthesis"

( x i ) SEQUENCE DESCRIPTION: SEQ ID NO: 29:

```
CGCGTCATCG CCTTTTTTAT ATTTCCTTT GT                                        32
```

( 2 ) INFORMATION FOR SEQ ID NO: 30:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: other nucleic acid ( A ) DESCRIPTION: /desc = "synthetic DNA from
oligonucleotide synthesis"

( x i ) SEQUENCE DESCRIPTION: SEQ ID NO: 30:

GACGCGAGTT ATTTTGAACC AACAGGCCGG CATG  34

( 2 ) INFORMATION FOR SEQ ID NO: 31:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "synthetic DNA from
        oligonucleotide synthesis"

( x i ) SEQUENCE DESCRIPTION: SEQ ID NO: 31:

CCGGCCTGTT GGTTCAAAAT AACT  24

( 2 ) INFORMATION FOR SEQ ID NO: 32:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "synthetic DNA from
        oligonucleotide synthesis"

( x i ) SEQUENCE DESCRIPTION: SEQ ID NO: 32:

ATTCAACTTA ATTACCAAGG TTGTTATAGA AAAGAAATAA CTGCA  45

( 2 ) INFORMATION FOR SEQ ID NO: 33:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "synthetic DNA from
        oligonucleotide synthesis"

( x i ) SEQUENCE DESCRIPTION: SEQ ID NO: 33:

GTTATTTCTT TTCTATAACA ACCTTGGTAA TTAAGTTG  38

( 2 ) INFORMATION FOR SEQ ID NO: 34:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "synthetic DNA from
        oligonucleotide synthesis"

( x i ) SEQUENCE DESCRIPTION: SEQ ID NO: 34:

AATTCGTCGA CGGTAAAAGA AATGAGCTCT TGTCCCCGCG GTATGT  46

( 2 ) INFORMATION FOR SEQ ID NO: 35:

( i ) SEQUENCE CHARACTERISTICS:
        ( A ) LENGTH: 41 base pairs ( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "synthetic DNA from oligonucleotide synthesis"

( x i ) SEQUENCE DESCRIPTION: SEQ ID NO: 35:

CATACCGCGG GGACAAGAGC TCATTTCTTT TACCGTCGAC G    41

( 2 ) INFORMATION FOR SEQ ID NO: 36:

( i ) SEQUENCE CHARACTERISTICS:
( A ) LENGTH: 27 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "synthetic DNA from oligonucleotide synthesis"

( x i ) SEQUENCE DESCRIPTION: SEQ ID NO: 36:

CGTATTTGVN AGTAAATGTG ACTGGAG    27

( 2 ) INFORMATION FOR SEQ ID NO: 37:

( i ) SEQUENCE CHARACTERISTICS:
( A ) LENGTH: 31 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "synthetic DNA from oligonucleotide synthesis"

( x i ) SEQUENCE DESCRIPTION: SEQ ID NO: 37:

TCGACTCCAG TCACATTTAC TNBCAAATAC G    31

( 2 ) INFORMATION FOR SEQ ID NO: 38:

( i ) SEQUENCE CHARACTERISTICS:
( A ) LENGTH: 27 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "synthetic DNA from oligonucleotide synthesis"

( x i ) SEQUENCE DESCRIPTION: SEQ ID NO: 38:

CGTATTTGBN CGTAAATGTG ACTGGAG    27

( 2 ) INFORMATION FOR SEQ ID NO: 39:

( i ) SEQUENCE CHARACTERISTICS:
( A ) LENGTH: 31 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "synthetic DNA from oligonucleotide synthesis"

( x i ) SEQUENCE DESCRIPTION: SEQ ID NO: 39:

TCGACTCCAG TCACATTTAC GNVCAAATAC G    31

(2) INFORMATION FOR SEQ ID NO: 40:

(i) SEQUENCE CHARACTERISTICS:
    (A) LENGTH: 21 base pairs
    (B) TYPE: nucleic acid
    (C) STRANDEDNESS: single
    (D) TOPOLOGY: linear (ii) MOLECULE TYPE: other nucleic acid
    (A) DESCRIPTION: /desc = "synthetic DNA from oligonucleotide synthesis"

(xi) SEQUENCE DESCRIPTION: SEQ ID NO: 40:

TGTAGTCCCA GGTTTAATAG G    21

TABLE 1

| Name of linker | Sequence of linkers from the 5'-end to the 3'-end |
|---|---|
| L1 | AGCT TGAATTCAGGAGGCCTCATATGT CAAG TTCAT |
| L2 | TCGA ATGAACTTGACATATGAGGCCTC CTGA ATTCA |
| L3 | ATTC AACTTAATTACAAGGTTGTTAT AGAA AAGAATAACTGCA |
| L4 | GTTA TTTCTTTTCTATAACAACCTTTG TAAT TAAGTTG |
| L5 | CCTC ATATGAAGGCGATGACG |
| L6 | CGTC ATCGCCTTCATATGAGG |
| L7 | CCTC ATATGGCGAGTTATTTTGAACCA CAGG |
| L8 | CCTG TGGTTCAAAATAACTCGCCATAT GAGG |
| L9 | AATT CAGGAGGCCTCATATGTCAAGTT CATT CGAAG |
| L10 | GATC CTTCGAATGAACTTGACATATGA GGCC TCCTG |
| L11 | CGAC AAAGGAAAATTTAAAAAAGGCGA T |
| L12 | CGCG TCATCGCCTTTTTTATATTTTCC TTTGT |
| L13 | GACG CGAGTTATTTTGAACCAACAGGC CGGC ATG |
| L14 | CCGG CCTGTTGGTTCAAAATAACT |
| L15 | ATTC AACTTAATTACCAAGGTTGTTAT AGAA AAGAATAACTGCA |
| L16 | GTTA TTTCTTTTCTATAACAACCTTGG TAAT TAAGTTG |
| L17 | AATT CGTCGACGGTAAAGAAATGAGC TCTT GTCCCCGCGGTATGT |
| L18 | CATA CCGCGGGGACAAAGAGCTCATTTC TTTT ACCGTCGACG |
| AG1 | CGTA TTTGCGAGTAAATGTGACTGGAG (branch: AGT / AC) |
| AG2 | TCGA CTCCAGTCACATTTACTCGCAAA (branch: ACGT / CTTT) |
| AG3 | TACG CGTA TTTGCCCGTAAATGTGACTGGAG (branch: GTG / ATT) |
| AG4 | TCGA CTCCAGTCACATTTACGCCCAAA (branch: AAGG / AGT) |
| SG 26 | TACG TGTA GTCCCAGGTTTAATAGG |

We claim:

1. A method for the recombinant production of a soluble staphylokinase having plasminogen activator activity, comprising culturing a host cell transformed with an expression vector comprising a DNA encoding a staphylokinase, wherein said DNA a) is free of a sequence encoding a signal peptide and b) is operatively linked to expression control sequences, in a medium under conditions wherein said DNA is expressed, and isolating said soluble staphylokinase from the cytoplasm of the host cell.

2. The method according to claim 1 wherein said host cell belongs to *E. coli*.

3. The method according to claim 1 wherein the target polypeptide is isolated by the following steps:
   a) lysing the host cell and separating resulting soluble components from resulting insoluble components,
   b) placing the soluble component directly onto an ion exchanger,
   c) selectively eluting target polypeptide present in the soluble component from the ion exchanger using an aqueous NaCl solution,
   d) subjecting the target polypeptide-containing eluate resulting from c) above, after enrichment with NaCl, directly to hydrophobic interaction chromatography using a hydrophobic interaction chromatography medium, and
   e) selectively eluting the target polypeptide from the hydrophobic interaction chromatography medium using a decreasing NaCl gradient and subsequently isolating the target polypeptide from the eluate.

4. The method according to claim 3, wherein the NaCl concentration in step
   c) is from 0 to 500 mM,
   d) is from 2.0 to 30 mM and
   e) is from 20 to 30 mM as initial concentration and from 15 to 100 mM as end concentration.

5. The method according to claim 1 or 3, further comprising formulating the isolated target polypeptide into a pharmaceutical composition.

6. The method according to claim 5, wherein said formulating is effected by combining the target polypeptide with a pharmaceutically acceptable diluent, adjuvant or carrier.

7. A DNA having a sequence encoding amino acid residues 1–136 of SEQ ID NO:14.

8. An isolated staphylokinase having the amino acid sequence encoded by the DNA of claim 7.

* * * * *